United States Patent
Auvin et al.

(10) Patent No.: US 9,975,880 B2
(45) Date of Patent: May 22, 2018

(54) IMIDAZOLIDINE-2,4-DIONE DERVATIVES

(71) Applicant: IPSEN PHARMA S.A.S., Boulogne-Billancourt (FR)

(72) Inventors: Serge Auvin, Palaiseau (FR); Christophe Lanco, Dourdan (FR); Oliver Dutruel, L'Hay les Roses (FR); Qi Chao, San Diego, CA (US); Kaichun Gu, Shanghai (CN)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days. days.

(21) Appl. No.: 15/108,746

(22) PCT Filed: Dec. 31, 2013

(86) PCT No.: PCT/CN2013/091118
§ 371 (c)(1),
(2) Date: Jun. 28, 2016

(87) PCT Pub. No.: WO2015/100617
PCT Pub. Date: Jul. 9, 2015

(65) Prior Publication Data
US 2016/0318908 A1    Nov. 3, 2016

(51) Int. Cl.
| | | |
|---|---|---|
| C07D 401/04 | (2006.01) | |
| C07D 401/14 | (2006.01) | |
| C07D 403/06 | (2006.01) | |
| C07D 403/14 | (2006.01) | |
| C07D 417/06 | (2006.01) | |
| C07D 417/14 | (2006.01) | |

(52) U.S. Cl.
CPC ......... *C07D 403/06* (2013.01); *C07D 401/14* (2013.01); *C07D 403/14* (2013.01); *C07D 417/06* (2013.01); *C07D 417/14* (2013.01)

(58) Field of Classification Search
CPC .......................... C07D 401/04; C07D 401/14
USPC ...................................... 546/274.1; 514/341
See application file for complete search history.

(56) References Cited

U.S. PATENT DOCUMENTS

| | | |
|---|---|---|
| 6,472,415 B1 | 10/2002 | Sovak et al. |
| 2005/0159468 A1 | 7/2005 | Cleve et al. |
| 2012/0095068 A1 | 4/2012 | Bigg et al. |

FOREIGN PATENT DOCUMENTS

| | | |
|---|---|---|
| WO | 1997000071 | 1/1997 |
| WO | 2007126765 | 8/2007 |

OTHER PUBLICATIONS

Simone, Oncology: Introduction, Cecil Textbook of Medicine, ed. Bennett et al. W.B. Saunders CO 20th ed. vol. 1, pp. 1004-1010. (Year: 1996).*
Gura, Systems for Identifying New Drugs Are Often Faulty, Cancer Models, Science, vol. 278, No. 5340, pp. 1041-1042. (Year: 1997).*
Johnson et al., "Relationships between, etc.," British Journal of Cancer, 64(10): 1424-1431. (Year: 2001).*
Golub et al., Molecular Classification, etc., Science, 286, 531-537. (Year: 1999).*
International Search Report dated Sep. 30, 2014 in PCT/CN2013/091118.

* cited by examiner

*Primary Examiner* — Patricia L Morris
(74) *Attorney, Agent, or Firm* — Hunton Andrews Kurth LLP

(57) ABSTRACT

Imidazolidine-2,4-dione derivatives of formula (I):

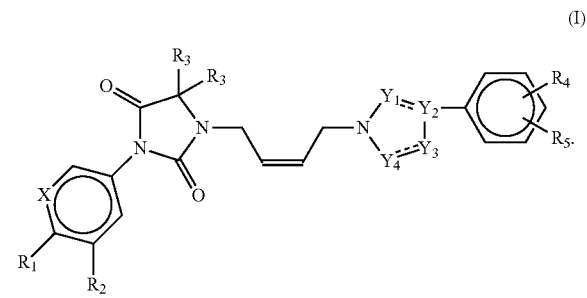

These compounds have anti-proliferative activity and are useful for treating pathological states and diseases linked to an abnormal cell proliferation, such as cancer.

10 Claims, No Drawings

IMIDAZOLIDINE-2,4-DIONE DERVATIVES

CROSS-REFERENCE TO RELATED APPLICATIONS

This application is the U.S. National Phase of International Patent Application No. PCT/CN2013/091118, filed Dec. 31, 2013, the contents of which are hereby incorporated by reference in their entirety.

FIELD OF THE INVENTION

A subject of the present application is novel imidazolidine-2,4-dione derivatives. These products have an anti-proliferative activity. They are particularly useful for treating the pathological states and the diseases linked to an abnormal cell proliferation such as cancers. The invention also relates to the pharmaceutical compositions containing said products and their use for the preparation of a medicament.

STATE OF THE ART

Nowadays, cancer still constitutes one of the major causes of death despite there being numerous molecules on the market.

It is therefore necessary to identify more powerful novel molecules allowing a better anti-tumour response, specifically by a good inhibitory activity on the proliferation of tumour cell colonies.

Such molecules are therefore particularly useful for treating the pathological states linked to an abnormal cell proliferation. They can therefore be used for the treatment of tumours or cancers, for example, those of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the connective tissues, the skin such as melanomas, the eyes, the brain and the central nervous system, as well as cancer of the thyroid gland, leukaemia, Hodgkin's disease, non-Hodgkin's lymphomas, multiple myelomas and other cancers.

It is of particular interest to find therapies for hormone-dependent cancers, for tumours expressing androgen receptors, for cancers of the breast and prostate.

The use of the anti-androgens in prostate cancer is based on their property of entering into competition with the natural agonists of the androgen receptor. However, the efficacy of these anti-androgens appears to be limited over time, the patients rapidly escaping the treatment. Several hypotheses regarding this failure have been developed showing an agonist activity in place of an antagonist activity of these molecules (Veldscholte J, Berrevoets CA, Brinkmann AO, Grootegoed JA, Mulder E. Biochemistry 1992 Mar. 3; 31(8):2393-9). For example, nilutamide is capable of stimulating the growth of human prostate cancer cells in culture. In addition to these experimental indications, clinical data also support this deleterious role of the anti-androgens (Akimoto S.; Antiandrogen withdrawal syndrome Nippon Rinsho. 1998 Aug; 56(8):2135-9. Paul R, Breul J. Antiandrogen withdrawal syndrome associated with prostate cancer therapies: incidence and clinical significance Drug Saf. 2000 Nov.; 23(5):381-90). Resistance to anti-androgen therapies can also occur through overexpression of the androgen receptor, which then becomes highly sensitive to low levels of androgens. Another way by which prostate cancer cells become resistant is via the emergence of mutations in the androgen receptor that becomes responsive to other kinds of steroids than androgens, or deletions of part of the androgen receptor, which then becomes constitutively activated.

In WO2010/119194 the Applicant had identified compounds showing an anti-proliferative activity for the prostatic tumour which does not show agonist activity at concentrations where the nilutamide behaves as an agonist. This difference in these compounds' behaviour with respect to proliferation compared with that of nilutamide is supported by their ability to induce the disappearance of androgen receptors in their protein form. Nilutamide has no effect on this receptor level. The properties of these molecules allow better management of prostate cancer avoiding the failure of current anti-androgens.

However, these molecules have a poor aqueous solubility, which makes them hard to formulate as an effective medicine. In fact, in pharmacokinetic studies in animals, the plasma exposure did not increase with dose due to the limited solubility in formulations.

Therefore there is a need to identify compounds showing a good anti-proliferative activity for the prostatic tumour, no escape from treatment and which can also be easily formulated, by having a better aqueous solubility.

The Applicant has identified new compounds showing an anti-proliferative activity for the prostatic tumour with no escape from treatment which surprisingly does show a good aqueous solubility.

The properties of these novel molecules must allow to easily formulate the compounds in pharmaceutically acceptable formulations while keeping the same biological profile.

Moreover, the compounds of the present invention can also be used for treating pathologies linked to the presence of androgen receptors such as for example benign prostatic hyperplasia, prostamegaly, acne, androgenic alopecia, hirsutism etc.

SUMMARY OF THE INVENTION

A subject of the invention is therefore the compounds of general formula (I)

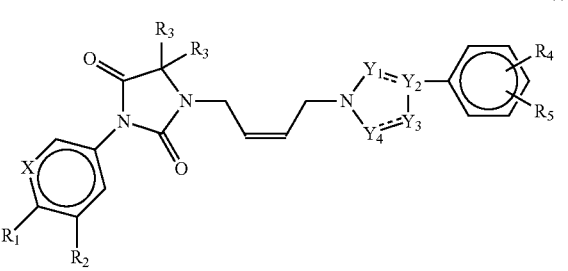

wherein,
$R^1$ is —CN, —$SO_2(C_1\text{-}C_6)$alkyl or —$SO_2(C_1\text{-}C_6)$cycloalkyl;
$R^2$ is —$CF_3$ or a halogen atom;
$R^3$ is $(C_1\text{-}C_6)$alkyl or the two $R^3$ together form a $(C_3\text{-}C_6)$cycloalkyl;
X is CH or N;
$Y^1$ is a carbon atom, a sulfonyl or a carbonyl group, it being understood that the carbon atom can be optionally substituted by one or more $(C_1\text{-}C_6)$ alkyl group;

Y² is a carbon atom, a nitrogen atom, it being understood that the carbon can be optionally substituted by a —OH group;

Y³ is a carbon atom, a nitrogen atom, it being understood that the carbon atom and the nitrogen atom can be optionally substituted by one or more (C₁-C₆) alkyl group;

Y⁴ is a carbon atom, a nitrogen atom, or a carbonyl group, it being understood that the carbon atom and the nitrogen atom can be optionally substituted by one or more (C₁-C₆) alkyl group;

R⁴ is H, alkyl, halogen, —CN or —SO₂(C₁-C₆)alkyl group;

R⁵ is H, —CF₃, a (C₁-C₆) alkyl group or a halogen atom;

each ⁻⁻⁻ is independently a single bond or a double bond;

or a pharmaceutically acceptable salt thereof.

Preferably, R¹ is a —SO₂(C₁-C₆)alkyl or —SO₂(C₁-C₆) cycloalkyl group. More preferably, R¹ is a —SO₂(C₁-C₂) alkyl group. Even more preferably, R¹ is a —SO₂ methyl group.

Alternatively, R¹ is a —CN group.

Preferably, R² is —CF₃.

Preferably, X is CH.

Preferably, R³ is a (C₁-C₆)alkyl group. More preferably R³ is a methyl group.

Preferably, R⁴ is a —SO₂(C₁-C₆)alkyl group. More preferably, R⁴ is a —SO₂ methyl group.

Alternatively, R⁴ is a —CN group.

Preferably, R⁵ is a —CF₃ group.

Preferably, Y⁴ is a nitrogen atom.

Alternatively, Y⁴ is a carbon atom.

Preferably, Y¹ is a carbon atom.

Alternatively, Y¹ is a carbonyl group.

Preferably, Y³ is a carbon atom.

Preferably, Y² is a carbon atom.

Alternatively, Y² is a nitrogen atom.

Preferably, only one of Y¹, Y², Y³ and Y⁴ is a nitrogen atom and the others are a carbon atom.

Preferably, Y⁴ is a nitrogen atom and Y¹, Y² and Y³ are a carbon atom.

Alternatively, Y² is a nitrogen atom and Y¹, Y³ and Y⁴ are a carbon atom.

Preferably, the two ⁻⁻⁻ are both a double bond.

Alternatively, the two ⁻⁻⁻ are both a single bond.

Preferably, R⁴ is in a para position on the phenyl ring.

Preferably, R⁵ is in a meta position on the phenyl ring.

In a preferred embodiment, the compound of formula I is chosen from:

(Z)-4-(3-(4-(4-(4-cyano-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile;

(Z)-4-(1-(4-(5,5-dimethyl-3-(4-(methylsulfonyl)-3-(trifluoromethyl)phenyl)-2,4-dioxoimidazolidin-1-yl)but-2-en-1-yl)-1H-pyrazol-4-yl)-2-(trifluoromethyl)benzonitrile;

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-1H-pyrazol-1-yl)but-2-en-1-yl)imidazolidine-2,4-dione;

(Z)-5-(4,4-dimethyl-3-(4-(4-(4-(methylsulfonyl)-3-(trifluoromethyl)phenyl)-1H-pyrazol-1-yl)but-2-en-1-yl)-2,5-dioxoimidazolidin-1-yl)-3-(trifluoromethyl)picolinonitrile;

(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile;

(Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile;

(Z)-4-(3-(4-(5,5-dimethyl-3-(4-(methylsulfonyl)-3-(trifluoromethyl)phenyl)-2-oxoimidazolidin-1-yl)but-2-en-1-yl)-4,4-dimethyl-2,5-dioxoimidazolidin-1-yl)-2-(trifluoromethyl)benzonitrile;

(Z)-3-(3-chloro-4-(methylsulfonyl)phenyl)-1-(4-(5,5-dimethyl-3-(4-(methylsulfonyl)-3-(trifluoromethyl)phenyl)-2-oxoimidazolidin-1-yl)but-2-en-1-yl)-5,5-dimethylimidazolidine-2,4-dione;

(Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2-oxoimidazolidin-1-yl)-2-(trifluoromethyl)benzonitrile;

(Z)-4-(4,4-dimethyl-3-(4-(3-(4-(methylsulfonyl)-3-(trifluoromethyl)phenyl)-2-oxoimidazolidin-1-yl)but-2-en-1-yl)-2,5-dioxoimidazolidin-1-yl)-2-(trifluoromethyl)benzonitrile;

(Z)-4-(3-(4-(3-(3-chloro-4-(methylsulfonyl)phenyl)-2-oxoimidazolidin-1-yl)but-2-en-1-yl)-4,4-dimethyl-2,5-dioxoimidazolidin-1-yl)-2-(trifluoromethyl)benzonitrile;

(Z)-4-(1-(4-(3-(4-cyano-3-(trifluoromethyl)phenyl)-5,5-dimethyl-2,4-dioxoimidazolidin-1-yl)but-2-en-1-yl)pyrrolidin-3-yl)-2-(trifluoromethyl)benzonitrile;

(Z)-4-(4,4-dimethyl-3-(4-(4-(4-(methylsulfonyl)-3-(trifluoromethyl)phenyl)-2-oxopyrrolidin-1-yl)but-2-en-1-yl)-2,5-dioxoimidazolidin-1-yl)-2-(trifluoromethyl)benzonitrile;

(Z)-4-(3-(4-(4-(3-chloro-4-(methylsulfonyl)phenyl)-2-oxopyrrolidin-1-yl)but-2-en-1-yl)-4,4-dimethyl-2,5-dioxoimidazolidin-1-yl)-2-(trifluoromethyl)benzonitrile;

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione;

(Z)-4-(1-(4-(3-(3-chloro-4-(methylsulfonyl)phenyl)-5,5-dimethyl-2,4-dioxoimidazolidin-1-yl)but-2-en-1-yl)-3-hydroxypyrrolidin-3-yl)-2-(trifluoromethyl)benzonitrile;

(Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile;

(Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile;

(Z)-4-(4,4-dimethyl-2,5-dioxo-3-(4-(4-phenyl-1H-1,2,3-triazol-1-yl)but-2-en-1-yl) imidazolidin-1-yl)-2-(trifluoromethyl)benzonitrile;

(Z)-4-(3-(4-(4-(3,4-dichlorophenyl)-1H-1,2,3-triazol-1-yl)but-2-en-1-yl)-4,4-dimethyl-2,5-dioxoimidazolidin-1-yl)-2-(trifluoromethyl)benzonitrile;

(Z)-4-(3-(4-(4-(4-fluoro-3-methylphenyl)-1H-1,2,3-triazol-1-yl)but-2-en-1-yl)-4,4-dimethyl-2,5-dioxoimidazolidin-1-yl)-2-(trifluoromethyl)benzonitrile; or (Z)-4-(3-(4-(4-(4-cyano-3-(trifluoromethyl)phenyl)-1H-1,2,3-triazol-1-yl)but-2-en-1-yl)-4,4-dimethyl-2,5-dioxoimidazolidin-1-yl)-2-(trifluoromethyl)benzonitrile;

or a pharmaceutically acceptable salt of this compound.

Preferably, the compound of formula I is:

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-1H-pyrazol-1-yl)but-2-en-1-yl)imidazolidine-2,4-dione;

(Z)-5-(4,4-dimethyl-3-(4-(4-(4-(methylsulfonyl)-3-(trifluoromethyl)phenyl)-1H-pyrazol-1-yl)but-2-en-1-yl)-2,5-dioxoimidazolidin-1-yl)-3-(trifluoromethyl)picolinonitrile;

(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile;

(Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile;

(Z)-4-(3-(4-(3-(3-chloro-4-(methylsulfonyl)phenyl)-2-oxoimidazolidin-1-yl)but-2-en-1-yl)-4,4-dimethyl-2,5-dioxoimidazolidin-1-yl)-2-(trifluoromethyl)benzonitrile;

(Z)-4-(3-(4-(4-(3-chloro-4-(methylsulfonyl)phenyl)-2-oxopyrrolidin-1-yl)but-2-en-1-yl)-4,4-dimethyl-2,5-dioxoimidazolidin-1-yl)-2-(trifluoromethyl)benzonitrile;

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione;

(Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile;

(Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile;

or a pharmaceutically acceptable salt thereof.

More preferably, the compound of formula I is:

(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile;

(Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile;

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione;

or a pharmaceutically acceptable salt thereof.

Another subject of the invention is a compound of formula I as defined above, as a medicament.

Another subject of the invention is a pharmaceutical composition containing, as active ingredient, at least one compound of formula (I) as defined above, in combination with a pharmaceutically acceptable support.

Another subject of the invention is the use of a compound of formula (I) as defined above, for the preparation of a medicament intended to treat cancers.

Preferably the medicament is intended to treat a hormone-dependent cancer.

More preferably, the medicament is intended to treat a cancer expressing androgen receptors.

More preferably, the medicament is intended to treat a breast or prostate cancer, preferably a prostate cancer.

DETAILED DESCRIPTION OF EMBODIMENTS OF THE INVENTION

Therefore a subject of the invention is the compounds of general formula (I) (I)
wherein:

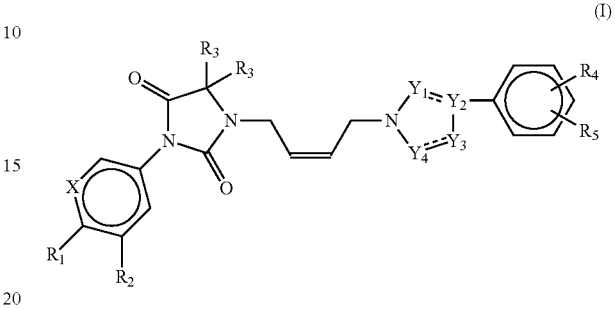

wherein,
$R^1$ is —CN, —SO$_2$(C$_1$-C$_6$)Alkyl or —SO$_2$(C$_1$-C$_6$)Cycloalkyl;
$R^2$ is —CF$_3$ or a halogen atom;
$R^3$ is (C$_1$-C$_6$)alkyl or the two $R^3$ together form a (C$_3$-C$_6$) cycloalkyl;
X is CH or N;
$Y^1$ is a carbon atom, a sulfonyl or a carbonyl group, it being understood that the carbon atom can be optionally substituted by one or more (C$_1$-C$_6$) alkyl group;
$Y^2$ is a carbon atom, a nitrogen atom, it being understood that the carbon can be optionally substituted by a —OH group;
$Y^3$ is a carbon atom, a nitrogen atom, it being understood that the carbon atom and the nitrogen atom can be optionally substituted by one or more (C$_1$-C$_6$) alkyl group;
$Y^4$ is a carbon atom, a nitrogen atom, or a carbonyl group, it being understood that the carbon atom and the nitrogen atom can be optionally substituted by one or more (C$_1$-C$_6$) alkyl group;
$R^4$ is H, Alkyl, Halogen, —CN or —SO$_2$(C$_1$-C$_6$)alkyl group;
$R^5$ is H, —CF$_3$, a (C$_1$-C$_6$) alkyl group or a halogen atom;
each ----- is independently a single bond or a double bond;
or a pharmaceutically acceptable salt thereof.

By pharmaceutically acceptable salt, is meant in particular addition salts of inorganic acids such as hydrochloride, hydrobromide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In the definitions indicated above, the expression halogen represents the fluoro, chloro, bromo or iodo radical, preferably chloro, fluoro or bromo. More preferably halogen represents the chloro radical.

Unless otherwise specified, the term alkyl within the meaning of the present invention represents a linear or branched alkyl radical comprising between 1 and 6 carbon atoms such as the methyl, ethyl, propyl, isopropyl, butyl, isobutyl, sec-butyl and tert-butyl, pentyl or amyl, isopentyl, neopentyl, hexyl or isohexyl radicals. The alkyl radical is a $(C_1-C_6)$alkyl radical, i.e. representing an alkyl radical having 1 to 6 carbon atoms as defined above, or preferably a $(C_1-C_4)$alkyl radical representing an alkyl radical having 1 to 4 carbon atoms such as for example the methyl, ethyl, propyl, isopropyl, butyl, isobutyl, sec-butyl and tert-butyl radicals. Very preferentially, the alkyl radical is the methyl radical. By cycloalkyl unless otherwise specified, is meant a saturated cyclic carbon radical comprising 3 to 6 members such as the cyclopropyl or cyclobutyl.

By $R^4$ is in a para position on the phenyl ring, is meant that $R^4$ is attached as follows:

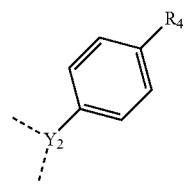

By $R^5$ is in a meta position on the phenyl ring, is meant that $R^5$ is attached as follows:

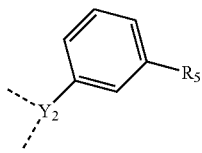

DETAILED DESCRIPTION OF THE PREPARATION PROCESSES

A) Preparation of compounds of general formula I

The compounds of general formula I can be prepared by different synthetic routes. For example, but not limitatively, they can be prepared according to one of the following routes.

A.1) Route 1

Compounds of general formula I as described above can be prepared as shown in scheme A.1 below. Compounds of formula I in which $R^1$, $R^2$, $R^3$, $R^4$, $R^5$, X, $Y^1$, $Y^2$, $Y^3$ and $Y^4$ are as defined above can be prepared by N-alkylation of a compound of general formula II.$_1$ in which $R^1$, $R^2$, $R^3$ and X are as defined above by a compound of general formula III.$_1$ in which $Y^1$, $Y^2$, $Y^3$, $Y^4$, $R^4$ and $R^5$ are as defined above. The reaction could be conducted at a temperature between 15 and 35° C., and in particular at room temperature. The reaction could be conducted in an aprotic solvent such as, for instance acetonitrile, dimethylformamide or tetrahydrofurane. The reaction could be conducted in presence of a mineral base such as $K_2CO_3$, $Na_2CO_3$, NaH or KH or an organic base such as a tertiary amine such as, for instance triethylamine.

Scheme A.1

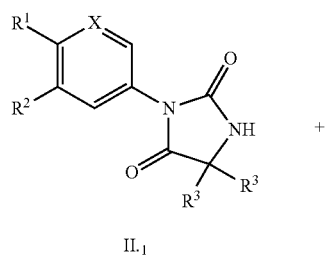

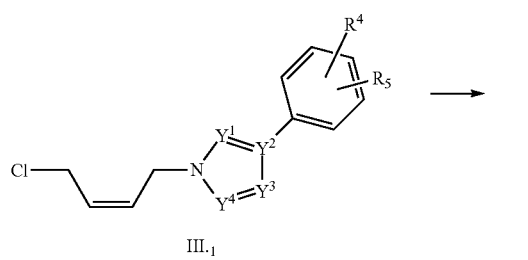

A.2) Route 2

Compounds of general formula I as described above can be prepared as shown in scheme A.2 below. Compounds of formula I in which $R^1$, $R^2$, $R^3$, $R^4$, $R^5$, X, $Y^1$, $Y^2$, $Y^3$ and $Y^4$ are as defined above can be prepared by N-alkylation of a compound of general formula III.$_2$ in which $Y^1$, $Y^2$, $Y^3$, $Y^4$, $R^4$ and $R^5$ are as defined above by a compound of general formula II.$_2$ in which $R^1$, $R^2$, $R^3$ and X are as defined above. The reaction could be conducted at a temperature between 15 and 35° C. For instance the reaction could be conduct at room temperature. The reaction could be conducted in an aprotic solvent such as, for instance acetonitrile, dimethylformamide or tetrahydrofurane. The reaction could be conducted in presence of a mineral base such as $K_2CO_3$, $Na_2CO_3$, NaH or KH or an organic base such as a tertiary amine such as, for instance triethylamine.

Scheme A.2

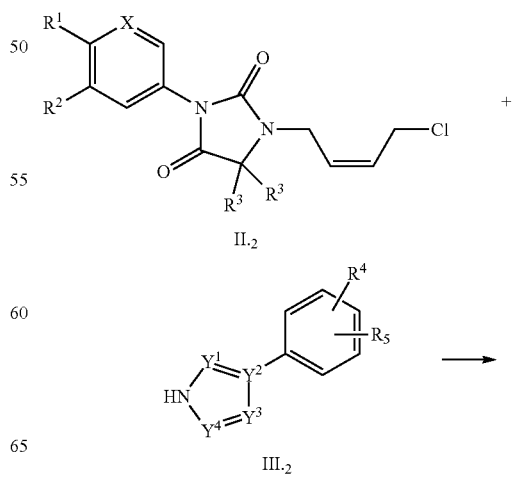

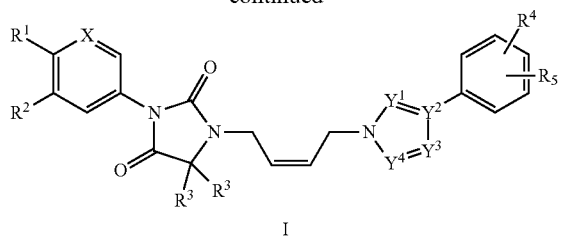 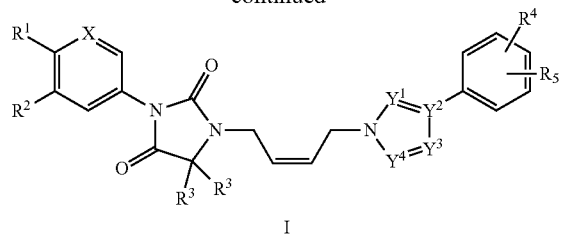

A.3) Route 3

(Compounds of Formula I Wherein $Y^2$ is Nitrogen, or Wherein $Y^1$ and $Y^2$ are Carbon Atoms)

Compounds of general formula I as described above can be prepared as shown in scheme A.3 below. Compounds of formula I in which, $R^2$, $R^3$, $R^4$, $R^5$, X, $Y^1$, $Y^2$, $Y^3$ and $Y^4$ are as defined above can be prepared:

i. By condensation of a compound of general formula $II._3$ in which $R^1$, $R^2$, $R^3$, X, $Y^1$, $Y^3$ and $Y^4$ are as defined above and in which $Y^2$ is a nitrogen atom and $Gf_1$ is an hydrogen atom and a compound of general formula $III._3$ in which $R^4$ and $R^5$ are as defined above and $Gf_2$ is a leaving group such as for instance a halogen atom. The reaction could be conducted at a temperature between 70 and 120° C. in an aprotic solvent such as for instance toluene in presence of a catalyst such as for instance a palladium complex such as for instance $Pd_2(dba)_3$.

ii. By reaction between a compound of general formula $II._3$ in which $R^1$, $R^2$, $R^3$, X, $Y^3$ and $Y^4$ are as defined above and in which $Y^1$ and $Y^2$ are carbon atoms and $Gf_1$ is a halogen atom and a compound of general formula $III._3$ in which $R^4$ and $R^5$ are as defined above and $Gf_2$ is a boronic ester. The reaction could be conducted at a temperature between 70 and 120° C. in an aprotic solvent such as for instance dioxane in the presence of a catalyst such as for instance a palladium complex such as for instance $Pd(dppf)_2Cl_2$ and a mineral base such as for instance potassium acetate.

A.4) Route 4

Compounds of general formula I as described above can be prepared as shown in scheme A.4 below. Compounds of formula I in which $R^1$, $R^2$, $R^3$, $R^4$, $R^5$, X, $Y^1$, $Y^2$, $Y^3$ and $Y^4$ are as defined above can be prepared by reaction of a compound of general formula $II._4$ in which $R^1$, $R^2$, $R^3$, $R^4$, $R^5$, X, $Y^3$ and $Y^4$ are as defined above and $Y^2$ is a nitrogen atom and a compound of general formula $III._4$ in which $Y^1$ is a carbonyl or a sulfonyl group and $Gf_1$ is a leaving group such as for instance a chlorine atom, an imidazolyl group or $NH_2$. The reaction could be conducted at a temperature between 0 and 100° C. such as for instance at room temperature in an aprotic solvent such as for instance dimethylformamide, tetrahydrofurane or acetonitrile. The reaction could be conducted in presence of a mineral base such as $K_2CO_3$, $Na_2CO_3$, NaH or KH or an organic base such as a tertiary amine such as, for instance triethylamine or pyridine.

Scheme A.4

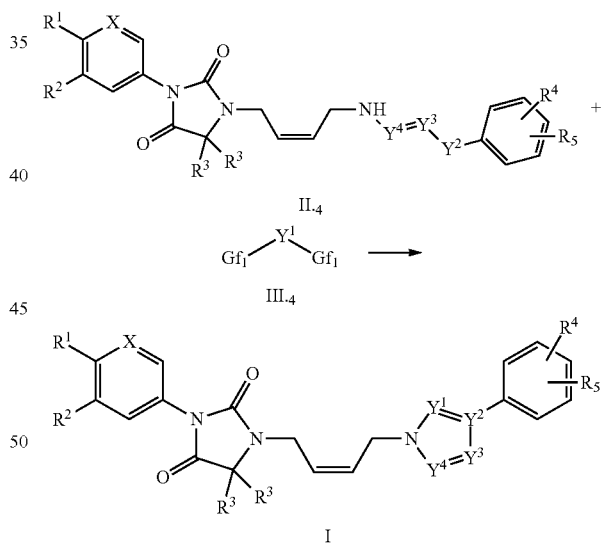

Scheme A.3

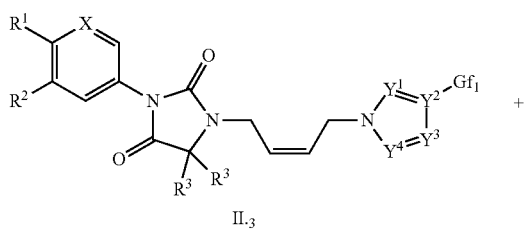

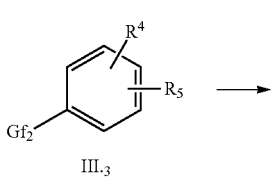

A.5) Route 5

Compounds of Formula I Wherein $Y^1$ and $Y^2$ are Carbon Atoms and $Y^3$ and $Y^4$ are Nitrogen Atoms)

Compounds of general formula I as described above can be prepared as shown in scheme A.5 below. Compounds of formula I in which $R^1$, $R^2$, $R^3$, $R^4$, $R^5$ and X are as defined above and in which $Y^1$ and $Y^2$ are carbon atoms and $Y^3$ and $Y^4$ are nitrogen atoms can be prepared by reaction between a compound of formula $II._5$ in which $R^1$, $R^2$, $R^3$ and X are as defined above and a compound of formula $III._5$ in which $R^4$ and $R^5$ are as defined above. The reaction could be conducted at a temperature between 0 and 100° C. such as for instance at room temperature. The reaction could be conducted in an aprotic solvent such as for instance in toluene in the presence of a copper catalyst such as for instance copper iodide and an organic base such as for instance diisopropylethylamine.

Scheme A.5

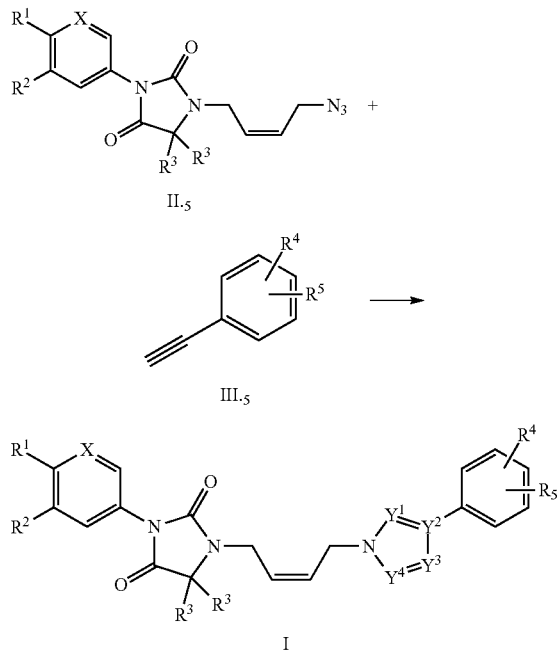

B) Preparation of compounds of general formula II

B.1) Preparation of compounds of general formula II.$_1$

Compounds of general formula II.$_1$ as described above can be prepared as shown in scheme B.1 below, according to i) or ii).

i. Compounds of general formula II.$_1$ in which $R^1$, $R^2$ and X are as defined above can be prepared by reaction of a hydantoin of general formula II.$_{1.2}$ in which $R^3$ is as defined above and a compound of general formula II.$_{1.1}$ in which $R^1$, $R^2$ and X are as defined above and Gf is an atom of iodine or bromine. The reaction could be conducted at a temperature between 80 and 150° C. in a polar aprotic solvent like for instance dimethylformamide. The reaction is conducted in presence of copper derivative such as for instance copper oxide.

ii. Compounds of general formula II.$_1$ in which $R^1$, $R^2$ and X are as defined above can be prepared by reaction of a hydantoin of general formula II.$_{1.2}$ in which $R^3$ is as defined above and a compound of general formula II.$_{1.1}$ in which $R^1$, $R^2$ and X are as defined above and Gf is an atom of fluorine. The reaction can be conducted in an aprotic solvent like for instance acetonitrile, dimethylformamide or tetrahydrofurane. The reaction is conducted in presence of a mineral or organic base. A convenient mineral base is for instance $K_2CO_3$, $Na_2CO_3$, NaH, or KH. A convenient organic base can be for instance a tertiary amine like for instance triethylamine or N,N,N-diisopropylethylamine.

Scheme B.1

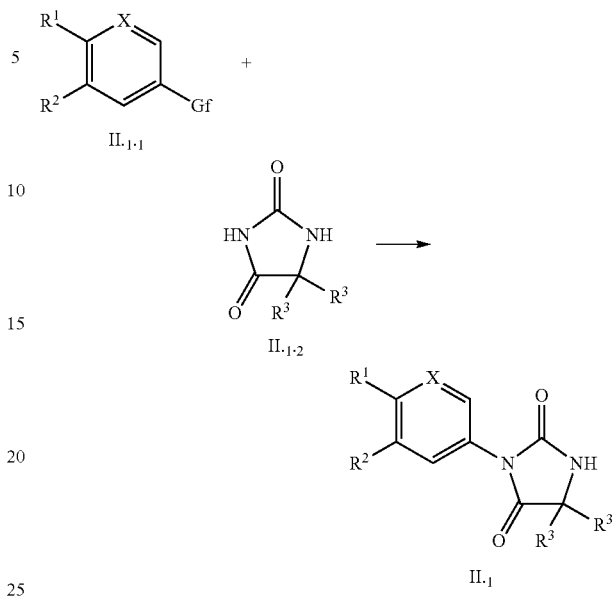

B.1.1) Preparation of compounds of general formula II.1.1

Compounds of general formula II.1.1 can be commercially available such as for instance 4-iodo-2-(trifluoromethyl)benzonitrile. Other compounds of general formula II.1.1 can be prepared as described below.

B.1.1.1) Preparation of compounds of general formula II.$_{1.1.1}$

Compounds of general formula II.$_{1.1.1}$ are a subclass of compounds of general formula II.$_{1.1}$ described above. Compounds of general formula II.$_{1.1.1}$ can be prepared as shown in scheme B.1.1.1 below. Compounds of formula II.$_{1.1.1}$ in which $R^2$ is as defined above, $R^7$ is an (C1-C6) alkyl group and Gf is a halogen atom could be prepared by treatment of a compound of general formula II.$_{1.1.1.1}$ in which $R^2$ is as defined above, $R^7$ is an (C1-C6) alkyl group and Gf is a halogen atom by an oxidizing agent such as for instance oxone. The reaction could be conducted at a temperature between 50 and 100° C. in a protic solvent such as for instance methanol or water.

Scheme B.1.1.1

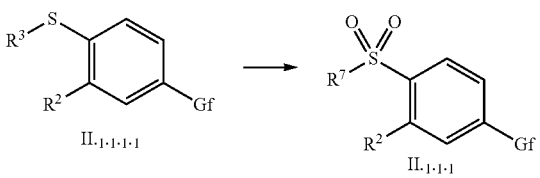

B.1.1.1.1) Preparation of compounds of general formula II.1.1.1.1

Compounds of general formula II.$_{1.1.1.1}$ as described above can be prepared as shown in scheme B.1.1.1.1 below. Compound of general formula II.$_{1.1.1.1}$ in which $R^2$ is as defined above, $R^7$ is an (C1-C6) alkyl group and Gf is a halogen atom can be prepared by treatment of a compound of general formula II.$_{1.1.1.1.1}$ in which $R^2$ is as defined above and Gf is a halogen atom by a compound of general formula $II._{1.1.1.1.2}$ in which $R^7$ is an (C1-C6) alkyl group. The reaction could be conducted in a polar aprotic solvent as for instance in dimethylformamide or in acetonitrile. The reaction could be conducted at a temperature between 20 and 100° C.

Scheme B.1.1.1.1

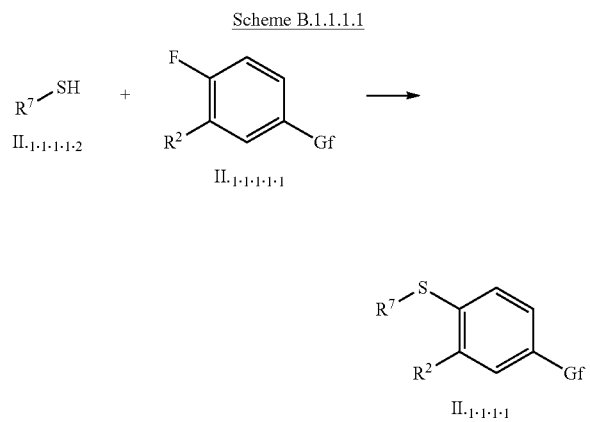

B.1.1.2) Preparation of compounds of general formula $II._{1.1.2}$

Compounds of general formula $II._{1.1.2}$ are a subclass of compounds of general formula $II._{1.1}$ described above. Compounds of general formula $II._{1.1.2}$ can be prepared as shown in scheme B.1.1.2 below. Compounds of general formula $II._{1.1.2}$ in which $R^2$ is as defined above and Gf is an iodine or a bromine atom can be prepared by treatment of a compound of general formula $II._{1.1.2.1}$ in which $R^2$ is as defined above and Gf is an iodine or a bromine atom by a cyanide salt such as for instance $Zn(CN)_2$. The reaction could be conducted at a temperature between 80 and 150° C. in a polar aprotic solvent like for instance dimethylformamide. The reaction could be conducted in the presence of a palladium complex derivative such as for instance $Pd_2(dba)_3$.

Scheme B.1.1.2

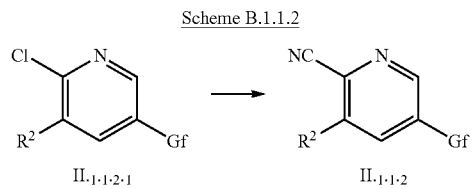

B.1.1.2.1) Preparation of compounds of general formula $III.1.2.1$

Compounds of general formula $II._{1.1.2.1}$ can be prepared as shown in scheme B.1.1.2.1 below. Compounds of general formula $II._{1.1.2.1}$ in which $R^2$ is as defined above and Gf is an iodine or a bromine atom can be prepared by treatment of a compound of general formula $II._{1.1.2.14}$ in which $R^2$ is as defined above and Gf is an iodine or a bromine atom by a chlorinating agent such as for instance $POCl_3$. The reaction could be conducted at a temperature between 100 and 150° C.

Scheme B.1.1.2.1

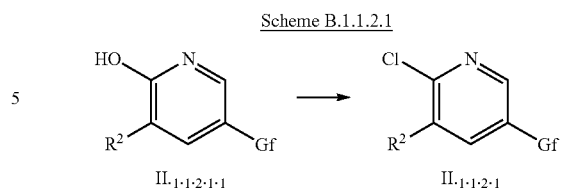

B.1.1.2.1.1) Preparation of compounds of general formula $II.1.1.2.1.1$

Compounds of general formula $II._{1.1.2.1.1}$ can be prepared as shown in scheme B.1.1.2.1.1 below. Compounds of general formula $II._{1.1.2.1.1}$ in which $R^2$ is as defined above and Gf is an iodine or a bromine atom can be prepared by treatment of a compound of general formula $II._{1.1.2.1.1.1}$ in which $R^2$ is as defined above such as 3-(trifluoromethyl)pyridin-2-ol which is commercially available by a halogenating agent such as for instance N-iodosuccinimide. The reaction could be conducted at a temperature between 50 and 130° C. in an aprotic polar solvent such as for instance dimethylformamide or acetonitrile.

Scheme B.1.1.2.1.1

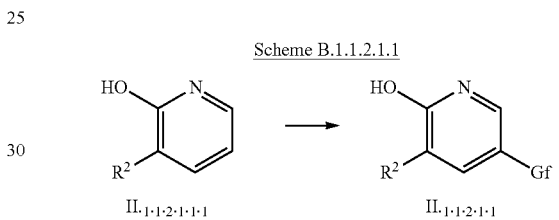

B.1.2) Preparation of hydantoins of general formula $II._{1.2}$

Non commercially available hydantoins of general formula $I._{1.2}$ in which $R^3$ is as defined above can be prepared following the methods described in the literature (e.g. *J. Med. Chem.* 1984, 27 (12), 1663-8)

B.2) Preparation of compounds of general formula $II._2$

Compounds of general formula $II._2$ as described above can be prepared as shown in scheme B.2 below. Compounds of formula $II._2$ in which $R^1$, $R^2$, $R^3$ and X are as defined above can be prepared by N-alkylation of a compound of general formula $II._1$ in which $R^1$, $R^2$, $R^3$ and X are as defined above by an excess of (Z)-1,4-dichlorobut-2-ene. The reaction could be conducted at a temperature between 15 and 35° C. For instance the reaction could be conducted at room temperature. The reaction could be conducted in a aprotic solvent like for instance acetonitrile, dimethylformamide or tetrahydrofurane. The reaction could be conducted in the presence of a mineral base such as $K_2CO_3$, $Na_2CO_3$, NaH or KH or an organic base such as a tertiary amine such as, for instance triethylamine.

Scheme B.2

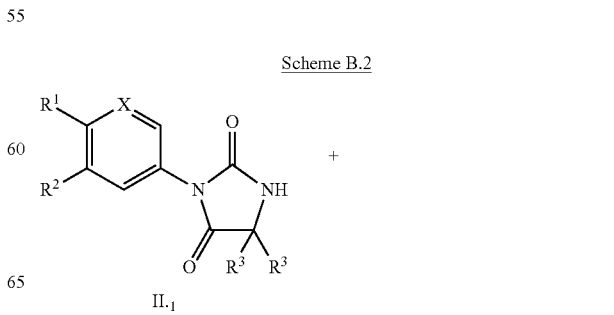

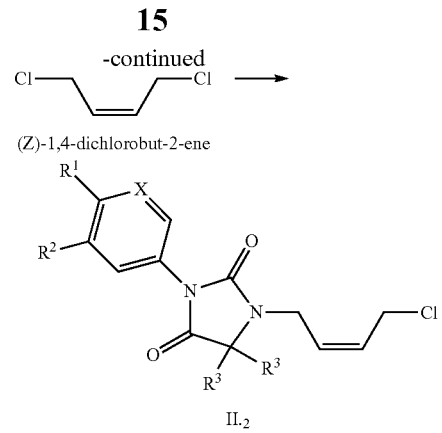

(Z)-1,4-dichlorobut-2-ene

B.3) Preparation of Compounds of General Formula II.$_3$

B.3.1) Preparation of compounds of general formula II.$_{3.1}$

Compounds of general formula II.$_{3.1}$ are a subclass of compounds of general formula II.$_3$ described above. Compounds of general formula II.$_{3.1}$ can be prepared as shown in scheme B.3.1 below. Compounds of formula II.$_{3.1}$ in which $R^1$, $R^2$, $R^3$, X, $Y^3$ and $Y^4$ are as defined above and Gf is a protecting group such as for instance a ter-butyloxycarbonyl group or a hydrogen atom can be prepared by reaction between a compound of general formula II.$_{3.1.1}$ in which $R^1$, $R^2$, $R^3$, X, $Y^3$, $Y^4$ and Gf are as defined above and a compound of general formula III.$_4$ in which $Y^1$ is a carbonyl or a sulfonyl group and Gf$_1$ is a leaving group such as for instance a chlorine atom, an imidazolyl group or NH$_2$. The reaction could be conducted at a temperature between 0 and 100° C. such as for instance at room temperature in an aprotic solvent such as for instance dimethylformamide, tetrahydrofurane or acetonitrile. The reaction could be conducted in presence of a mineral base such as K$_2$CO$_3$, Na$_2$CO$_3$, NaH or KH or an organic base such as a tertiary amine such as, for instance triethylamine or pyridine.

Scheme B.3.1

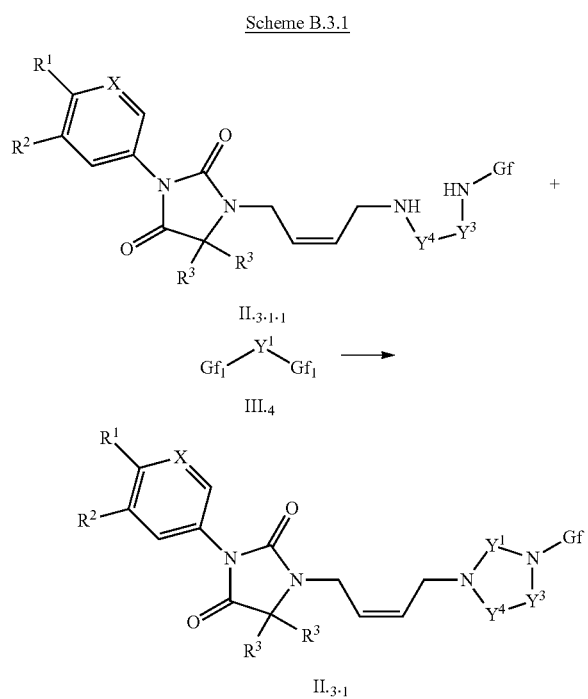

B.3.1.1) Preparation of compounds of general formula II.$_{3.1.1}$

Compounds of general formula II.$_{3.1.1}$ can be prepared as shown in scheme B.3.1.1 below. Compounds of general formula II.$_{3.1.1}$ in which $R^1$, $R^2$, $R^3$, X, $Y^3$ and $Y^4$ are as defined above and in which Gf is a tert-butyloxycarbonyl group or a hydrogen atom can be prepared by alkylation of a compound of general formula II.$_{3.1.1.1}$ in which $Y^3$ and $Y^4$ are as defined above and in which Gf is a tert-butyloxycarbonyl group or a hydrogen atom by a compound of general formula II.$_2$ in which $R^1$, $R^2$, $R^3$ and X are as defined above. The reaction could be conducted at a temperature between 15 and 35° C. For instance the reaction could be conducted at room temperature. The reaction could be conducted in an aprotic solvent such as, for instance acetonitrile, dimethylformamide or tetrahydrofurane. The reaction could be conducted in presence of a mineral base such as K$_2$CO$_3$, Na$_2$CO$_3$, NaH or KH or an organic base such as a tertiary amine such as, for instance triethylamine.

Scheme B.3.1.1

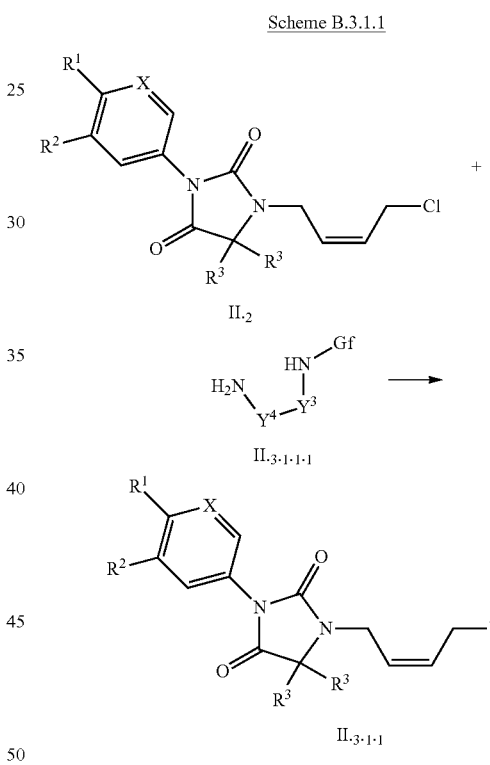

B.3.2) Preparation of compounds of general formula II.$_{3.2}$

Compounds of general formula II.$_{3.2}$ are a subclass of compounds of general formula II.$_3$ described above. Compounds of general formula II.$_{3.2}$ can be prepared as shown in scheme B.3.2 below. Compounds of general formula II.$_{3.2}$ in which $R^1$, $R^2$, $R^3$, X are as defined above and $Y^3$ and $Y^4$ are a carbon atom or a nitrogen atom can be prepared by alkylation of a compound of the general formula II.$_{3.2.1}$ in which $Y^3$ and $Y^4$ are a carbon atom or a nitrogen atom and Gf is a leaving group such as for instance a halogen atom by a compound of general formula II.$_2$ in which $R^1$, $R^2$, $R^3$ and X are as defined above. The reaction could be conducted at a temperature between 15 and 35° C. The reaction could be conducted in an aprotic solvent such as, for instance acetonitrile, dimethylformamide or tetrahydrofurane. The reaction could be conducted in presence of a mineral base such as $K_2CO_3$, $Na_2CO_3$, NaH or KH or an organic base such as a tertiary amine such as, for instance triethylamine.

Scheme B.3.2

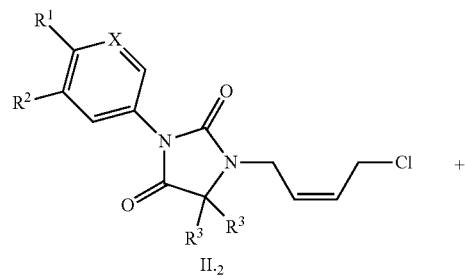

II.$_2$

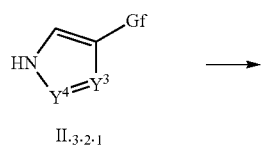

II.$_{3-2-1}$

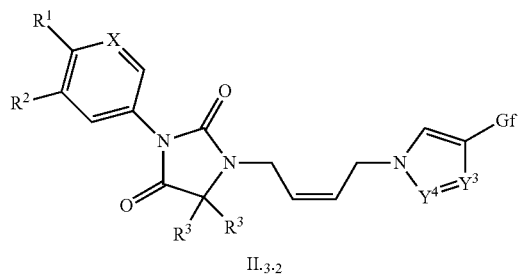

II.$_{3-2}$

B.4) Preparation of compounds of general formula II.$_4$

Compounds of general formula II.$_4$ can be prepared as shown in scheme B.4 below. Compounds of general formula II.$_4$ in which $R^1$, $R^2$, $R^3$, X, $Y^3$ and $Y^4$ are as defined above can be prepared by alkylation of a compound of the general formula II.$_{4.1}$ in which $Y^3$ and $Y^4$ are as defined above by a compound of general formula II.$_2$ in which $R^1$, $R^2$, $R^3$ and X are as defined above. The reaction could be conducted at a temperature between 15 and 35° C. The reaction could be conducted in an aprotic solvent such as, for instance acetonitrile, dimethylformamide or tetrahydrofurane. The reaction could be conducted in presence of a mineral base such as $K_2CO_3$, $Na_2CO_3$, NaH or KH or an organic base such as a tertiary amine such as, for instance triethylamine.

Scheme B.4

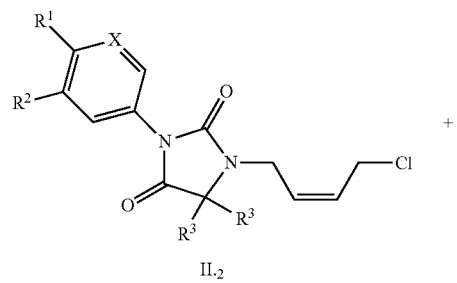

II.$_2$

-continued

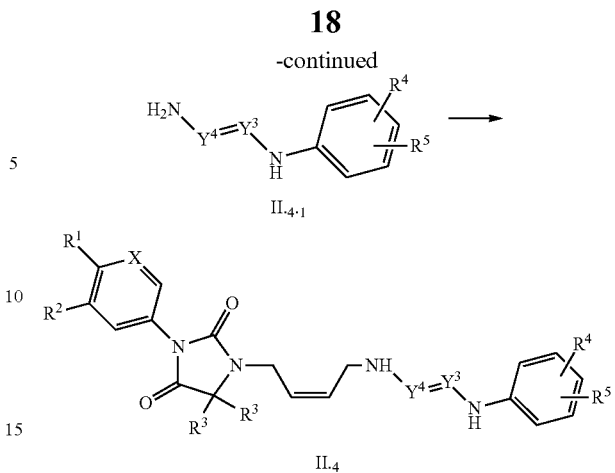

B.4.1) Preparation of compounds of general formula II.$_{4.1}$

Compounds of general formula II.$_{4.1}$ can be prepared as shown in scheme B.4.1 below. Compounds of general formula II.$_{4.1}$ in which $R^4$, $R^5$, $Y^3$ and $Y^4$ are as defined above can be prepared by reaction of a compound of the general formula II.$_{4.1.1}$ in which $Y^3$ and $Y^4$ are as defined above and a compound of the general formula III.$_3$ in which $R^4$ and $R^5$ are as defined above and Gf is a leaving group such as for instance a halogen atom. The reaction could be conducted at a temperature between 15 and 35° C. The reaction could be conducted in an aprotic solvent such as, for instance acetonitrile, dimethylformamide or tetrahydrofurane. The reaction could be conducted in presence of a mineral base such as $K_2CO_3$, $Na_2CO_3$, NaH or KH or an organic base such as a tertiary amine such as, for instance triethylamine.

Scheme B.4.1

B.5) Preparation of compounds of general formula II.$_5$

Compounds of general formula II.$_5$ can be prepared as shown in scheme B.5 below. Compounds of general formula II.$_5$ in which $R^1$, $R^2$, $R^3$ and X are as defined above can be prepared by reaction of a compound of the general formula II.$_2$ in which $R^1$, $R^2$, $R^3$ and X are as defined above and an azide salt such as for instance sodium azide salt. The reaction could be conducted at a temperature between 0 and 50° C. such as for instance at room temperature. The reaction could be conducted in an aprotic polar solvent such as, for instance acetonitrile, dimethylformamide or tetrahydrofurane.

Scheme B.5

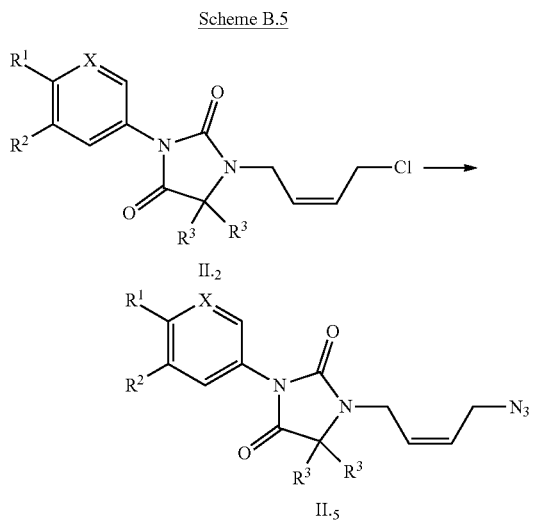

C) Preparation of compounds of general formula III

C.1) Preparation of compounds of general formula III.$_1$

Compounds of general formula III.$_1$ can be prepared as shown in scheme C.1 below. Compounds of general formula III.$_1$ in which $R^4$, $R^5$, $Y^1$, $Y^2$, $Y^3$ and $Y^4$ are as defined above can be prepared by N-alkylation of a compound of general formula III.$_2$ in which $R^4$, $R^5$, $Y^1$, $Y^2$, $Y^3$ and $Y^4$ are as defined above by an excess of (Z)-1,4-dichlorobut-2-ene. The reaction could be conducted at a temperature between 15 and 35° C. For instance the reaction could be conduct at room temperature. The reaction could be conducted in an aprotic solvent like for instance acetonitrile, dimethylformamide or tetrahydrofurane. The reaction could be either conducted in the presence of a mineral base such as $K_2CO_3$, $Na_2CO_3$, NaH or KH or an organic base such as a tertiary amine such as, for instance triethylamine.

Scheme C.1

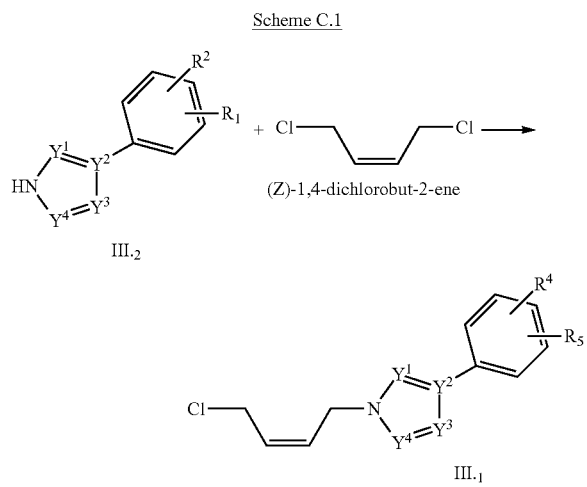

C.2) Preparation of compounds of general formula III.$_2$

C.2.1) Preparation of compounds of general formula III.$_{2.1}$ iii. Compounds of general formula III.$_{2.1}$ are a subclass of compounds of general formula III.$_2$ described above. Compounds of general formula III.$_{2.1}$ can be prepared as shown in scheme C.2.1 below. Compounds of general formula III.$_{2.1}$ in which $R^4$, $R^5$ and $Y^4$ are as defined above can be prepared by reaction between a compound of the general formula III.$_{2.1.1}$ in which $Y^4$ is as defined above and $Gf_1$ is a boronic ester and a compound of the general formula III.$_3$ in which $R^4$ and $R^5$ are as defined above and $Gf_2$ is a halogen atom. The reaction could be conducted at a temperature between 70 and 120° C. in an aprotic solvent such as for instance dioxane in the presence of a catalyst such as for instance a palladium complex such as for instance $Pd(PPh_3)_4$ and a mineral base such as for instance $K_2CO_3$.

Scheme C.2.1

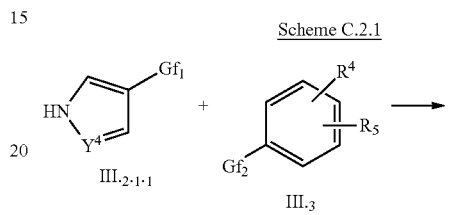

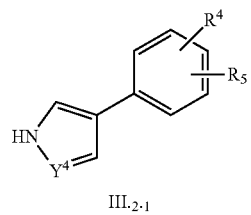

C.2.2) Preparation of compounds of general formula III.$_{2.2}$

Compounds of general formula III.$_{2.2}$ are a subclass of compounds of general formula III.$_2$ described above. Compounds of general formula III.$_{2.2}$ can be prepared as shown in scheme C.2.2 below. Compounds of general formula III.$_{2.2}$ in which $R^4$ and $R^5$ are as described above can be prepared by deprotection of a compound of the general formula III.$_{2.2.1}$ in which $R^4$ and $R^5$ are as described above and $Gf_1$ is a protecting group such as for instance a tert-butyloxycarbonyl group. For more examples of potential protecting group and methods see Greene's Protective Groups in Organic Synthesis.

Scheme C.2.2

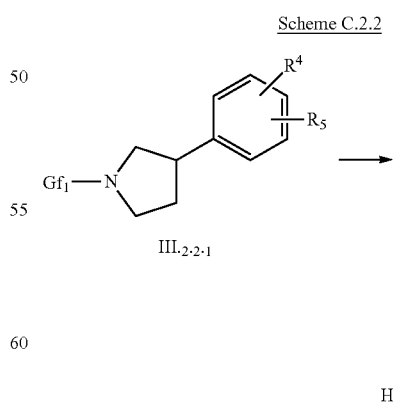

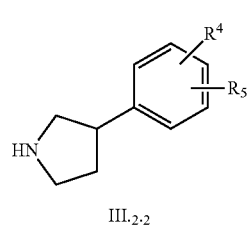

C.2.2.1) Preparation of compounds of general formula III.-2.2.1

Compounds of general formula III.-2.2.1 can be prepared as shown in scheme C.2.2.1 below. Compounds of general formula III.-2.2.1 in which $R^4$ and $R^5$ are as described above and Gf1 is a protecting group such as for instance a tert-butyloxycarbonyl group can be prepared by reduction of a mixture of compounds of general formulas $III_{a.2.2.1.1}$ and $III_{b.2.2.1.1}$ in which $R^4$ and $R^5$ are as described above and $Gf_1$ is a protecting group such as for instance a tert-butyloxycarbonyl group. The reaction could be conducted in a solvent such as for instance THF under an atmosphere of hydrogen and in the presence of a catalyst such as for instance palladium on carbon.

Scheme C.2.2.1

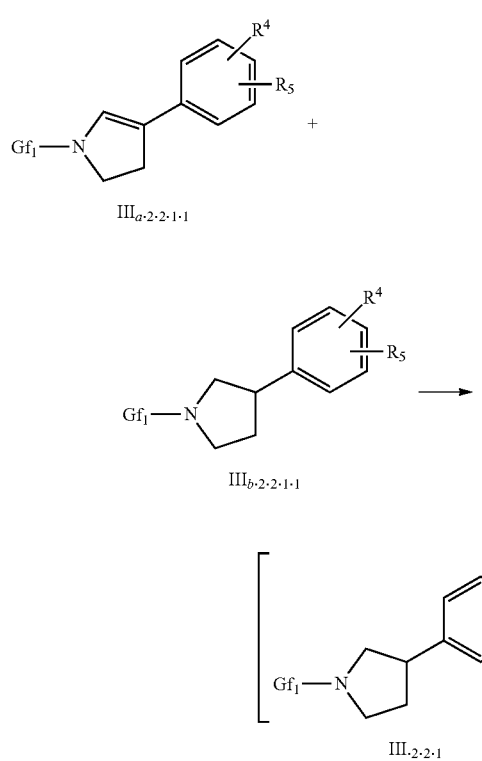

Scheme C.2.2.1.1

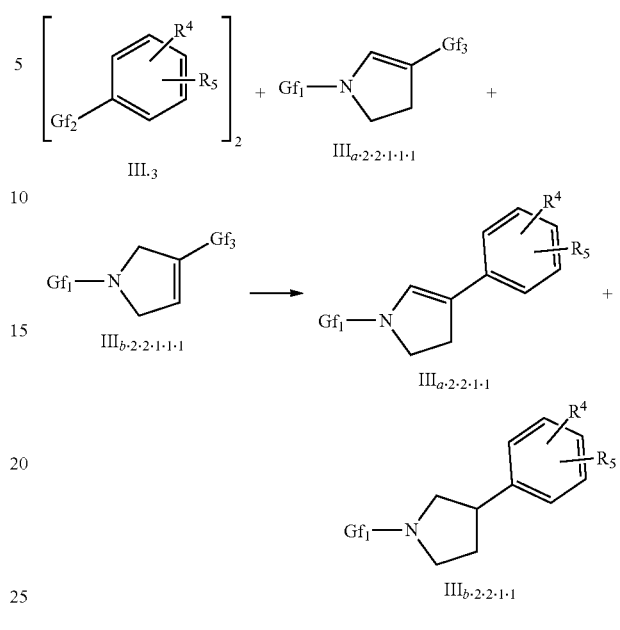

C.2.2.1.1) Preparation of compounds of general formula $III_{a.2.2.1.1}$ and $III_{b.2.2.1.1}$ Compounds of general formulas $III_{a.2.2.1.1}$ and $III_{b.2.2.1.1}$ can be prepared as shown in scheme C.2.2.1.1 below. Compounds of general formulas $III_{a.2.2.1.1}$ and $III_{b.2.2.1.1}$ in which $R^4$ and $R^5$ are as described above and $Gf_1$ is a protecting group such as for instance a tert-butyloxycarbonyl group can be prepared by reaction of two equivalents of a compound of the general formula $III._3$ in which $R^4$ and $R^5$ are as described above and $Gf_2$ is a halogen atom and a mixture of compounds of general formulas $III_{a.2.2.1.1.1}$ and $III._{2.2.1.1.1}$ in which $Gf_1$ is a protecting group such as for instance a tert-butyloxycarbonyl group and $Gf_3$ is a boronic ester. The reaction could be conducted at a temperature between 70 and 120° C. in an aprotic solvent such as for instance dioxane in the presence of a catalyst such as for instance a palladium complex such as for instance $Pd(PPh_3)_4$ and a mineral base such as for instance $K_2CO_3$.

C.2.2.1.1.1) Preparation of compounds of general formula $III_{a.2.2.1.1.1}$ and $III_{b.2.2.1.1.1}$ Compounds of general formulas $III_{a.2.2.1.1.1}$ and $III_{b.2.2.1.1.1}$ can be prepared as shown in scheme C.2.2.1.1.1 below. Compounds of general formulas $III_{a.2.2.1.1.1}$ and $III_{b.2.2.1.1.1}$ in which $Gf_1$ is a protecting group such as for instance a tert-butyloxycarbonyl group and $Gf_3$ is a boronic ester can be prepared by reaction of compounds of general formulas $III_{a.2.2.1.1.1.1}$ and $III_{b.2.2.1.1.1.1}$ in which $Gf_1$ is a protecting group such as for instance a tert-butyloxycarbonyl group and $Gf_2$ is a leaving group such as for instance a trifluoromethylsulfonyloxy group and a borylation reagent such as for instance 4,4,4',4',5,5,5',5'-octamethyl-2,2'-bis(1,3,2-dioxaborolane). The reaction can be conducted at a temperature between 50 and 120° C. in an aprotic solvent such as for instance 1,4-dioxane. The reaction is conducted in the presence of a catalyst such as for instance $Pd(dppf)_2Cl_2$ and a mineral base such as for instance Potassium acetate Scheme C.2.2.1.1.1

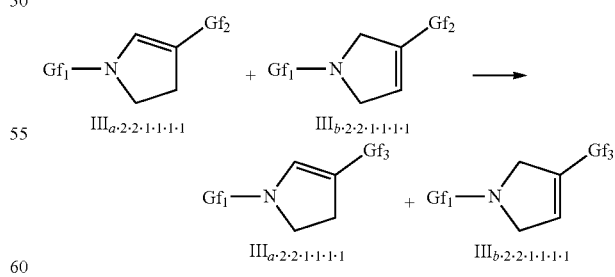

C. 2.2.1.1.1.1) Preparation of compounds of formula $III_{a.2.2.1.1.1.1}$ and $III._{2.2.1.1.1.1}$ Compounds of general formulas $III_{a.2.2.1.1.1.1}$ and $III_{b.2.2.1.1.1.1}$ can be prepared as shown in the scheme C.2.2.1.1.1.1 below. Compounds of general formula $III_{a.2.2.1.1.1.1}$ and $III_{b.2.2.1.1.1.1}$ in which $Gf_1$ is a protecting group such as for instance a tert-butyloxycarbonyl group and $Gf_2$ is a leaving group such as for instance a trifluoromethylsulfonyloxy group can be prepared from a compound of the general formula $III._{2.2.1.1.1.1.1}$ in which $Gf_1$ is a protecting group by all methods allowing the transformation of a ketone in a leaving group such as for instance by reaction with N-phenylbis(trifluoromethanesulfonimide). The reaction can be conducted in an aprotic solvent such as for instance THF at a temperature between −78° C. and room temperature. The reaction can be conducted in presence of a base such as for instance lithium bis(trimethylsilyl)amide.

Scheme C.2.2.1.1.1.1

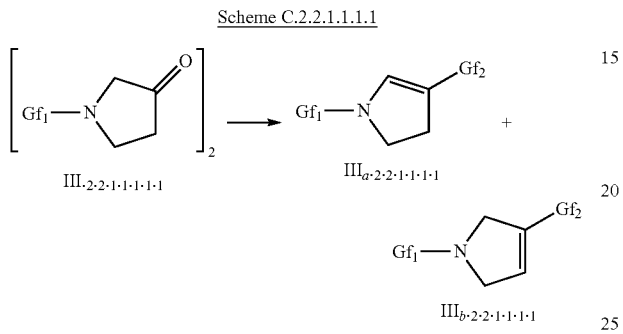

C.2.3) Preparation of compounds of general formula $III._{2.3}$

Compounds of general formula $III._{2.3}$ are a subclass of compounds of general formula $III._2$ described above. Compounds of general formula $III._{2.3}$ can be prepared as shown in scheme C.2.3 below. Compounds of general formula $III._{2.3}$ in which $R^4$ and $R^5$ are as described above can be prepared by reduction and cyclisation of a compound of the general formula $III._{2.3.1}$ in which $R^4$ and $R^5$ are as described above and $R^8$ is an alkyl group such as for instance a methyl or ethyl group by a reducing agent such as for instance hydrogen or iron in a solvent such as for instance acetic acid.

Scheme C.2.3

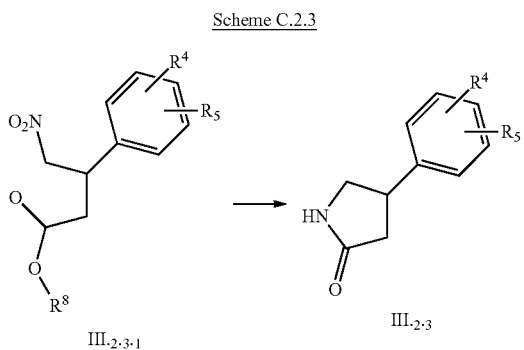

C.2.3.1) Preparation of compounds of general formula $III._{2.3.1}$

Compounds of general formula $III._{2.3.1}$ can be prepared as shown in the scheme C.2.3.1 below. Compounds of general formula $III._{2.3.1}$ in which $R^4$ and $R^5$ are as described above and $R^8$ is an alkyl group such as for instance a methyl or ethyl group can be prepared by alkylation of a compound of the general formula $III._{2.3.1.1.1}$ in which $R^4$ and $R^5$ are as described above and $R^8$ is an alkyl group such as for instance a methyl or ethyl group by nitromethane. The reaction can be conducted in an aprotic solvent or directly in nitromethane in presence of a base such as for instance 1,8-diazabicyclo[5.4.0]undec-7-ene.

Scheme C.2.3.1

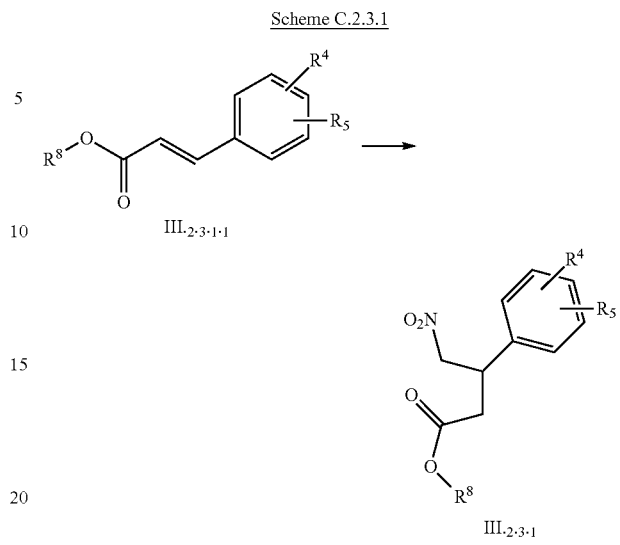

C.2.3.1.1) Preparation of compounds of general formula $III._{2.3.1.1}$

Compounds of general formula $III._{2.3.1.1}$ can be prepared as shown in the scheme C.2.3.1.1 below. Compounds of general formula $III._{2.3.1.1}$ in which $R^4$ and $R^5$ are as described above and $R^8$ is an alkyl group such as for instance a methyl or ethyl group can be prepared by reaction of a compound of the general formula $III._{2.3.1.1.1}$ in which $R^8$ is an alkyl group such as for instance a methyl or ethyl group and a compound of the general formula $III._3$ in which $R^4$ and $R^5$ are as described above and $Gf_1$ is a halogen atom. The reaction can be conducted in presence of a palladium catalyst such as for instance palladium acetate in an aprotic polar solvent such as for instance dimethylformamide in presence of a base such as for instance potassium acetate.

Scheme C.2.3.1.1

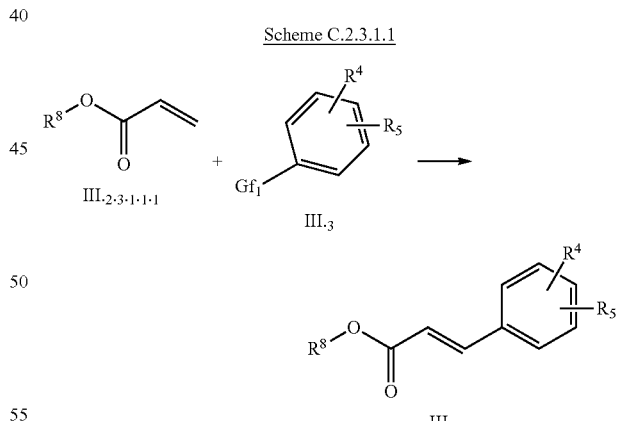

C.2.4) Preparation of compounds of general formula $III._{2.4}$

Compounds of general formula $III._{2.4}$ are a subclass of compounds of general formula $III._2$ described above. Compounds of general formula $III._{2.4}$ can be prepared as shown in scheme C.2.4 below. Compounds of general formula $III._{2.4}$ in which $R^4$ and $R^5$ are as defined above can be prepared by deprotection of a compound of the general formula $III._{2.4.1}$ in which $R^4$ and $R^5$ are as described above and $Gf_1$ is a protecting group such as for instance a tert-butyloxycarbonyl group. For more examples of potential protecting group and methods see Greene's Protective Groups in Organic Synthesis.

Scheme C.2.4

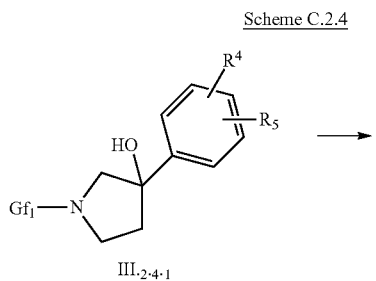

III.$_{\cdot 2\cdot 4\cdot 1}$

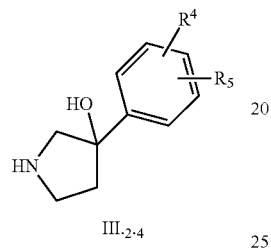

III.$_{\cdot 2\cdot 4}$

C.2.4.1) Preparation of compounds of general formula III.$_{\cdot 2.4.1}$

Compounds of general formula III.$_{\cdot 2.4.1}$ can be prepared as shown in scheme C.2.4.1 below. Compounds of general formula III.$_{\cdot 2.4.1}$ in which $R^4$ and $R^5$ are as defined above can be prepared by α-hydroxyalkylation of a compound of the general formula III.$_{\cdot 2.2.1.1.1.1.1}$ in which $Gf_1$ is a protecting group such as for instance a tert-butyloxycarbonyl group by a compound of general formula III.$_{\cdot 3}$ in which $R^4$ and $R^5$ are as defined above and $Gf_1$ is a protecting group such as for instance a tert-butyloxycarbonyl group and $Gf_2$ is a halogen atom. The reaction can be conducted in an aprotic solvent such as for instance THF at a temperature between −50° C. and room temperature. The reaction can be conducted in presence of a strong base such as for instance butyl lithium.

Scheme C.2.4.1

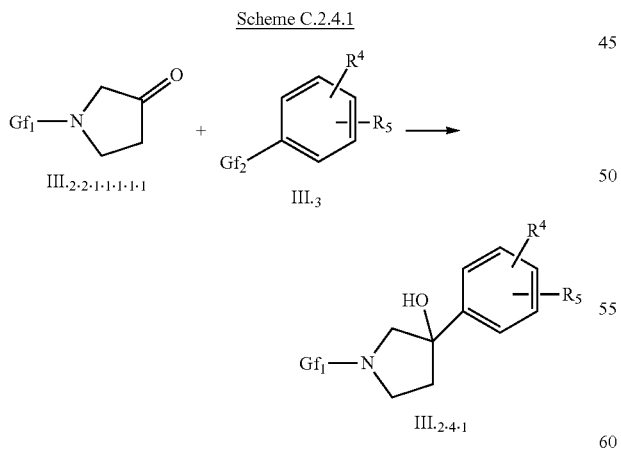

C.3) Preparation of compounds of general formula III.$_{\cdot 3}$

Compounds of general formula III.$_{\cdot 3}$ could be commercially available such as 4-iodo-2-(trifluoromethyl)benzonitrile or prepared following the procedure described for the synthesis of compounds of general formula II.$_{\cdot 1.1.1}$ in chapter B.1.1.1.

C.4) Preparation of compounds of general formula III.$_{\cdot 4}$

Compounds of general formula III.$_{\cdot 4}$ are commercially available such as for instance di(1H-imidazol-1-yl)methanone, phosgene or sulfuric diamide.

C.5) Preparation of compounds of general formula III.$_{\cdot 5}$

Compounds of general formula III.$_{\cdot 5}$ can be prepared as shown in the scheme C.5 below. Compounds of general formula III.$_{\cdot 5}$ in which $R^4$ and $R^5$ are as described above can be prepared by deprotection of a compound of the general formula III.$_{\cdot 5.1}$. The reaction can be conducted in a polar protic solvent such as for instance methanol in presence of a mineral base such as for instance potassium carbonate. The reaction can be conducted at a temperature between 0 and 50° C. such as for instance at room temperature.

Scheme C.5

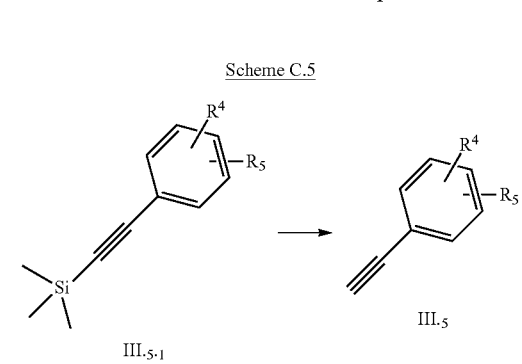

C.5.1) Preparation of compounds of general formula III.$_{\cdot 5.1}$

Compounds of general formula III.$_{\cdot 5.1}$ can be prepared as shown in the scheme C.5.1 below. Compounds of general formula III.$_{\cdot 5.1}$ in which $R^4$ and $R^5$ are as defined above can be prepared by alkylation of a compound of the general formula III.$_{\cdot 3}$ in which $R^4$ and $R^5$ are as defined above and Gf is a halogen atom by ethynyltrimethylsilane. The reaction can be conducted in the presence of a palladium catalyst such as for instance PdCl$_2$(Ph$_3$)$_2$ and copper salt such as for instance copper iodide and a base such as for instance triethylamine. The reaction can be conducted in an aprotic polar solvent such as for instance tetrahydrofurane.

Scheme C.5.1

A subject of the present application is also the use of a compound of formula (I) according to the present invention, for the preparation of a medicament intended to treat proliferative diseases, preferentially cancers, very preferentially hormone-dependent cancers or cancers expressing androgen receptors, or prostate and breast cancers and very preferentially prostate cancers.

The pharmaceutical composition can be in the form of a solid, for example powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water added to pharmaceutically acceptable oils or fats. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

Experimental Part

Following the definitions of the variables $R^1$, $R^2$, $R^3$, $R^4$, $R^5$, $Y^1$, $Y^2$, $Y^3$, $Y^4$ and X, the compounds according to the invention can be prepared according to the different methods described above.

The NMR analyses of Examples 1 to 22 were carried out on a 400 MHz Bruker-Avance II spectrometer.

The examples are presented in order to illustrate the above procedures and should in no event be considered as a limit to the scope of the invention.

The terminology used for the nomenclature of the compounds below and the examples is the IUPAC terminology.

Example 1

(Z)-4-(3-(4-(4-(4-cyano-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile Step A. 4-(4,4-dimethyl-2,5-dioxoimidazolidin-1-yl)-2-(trifluoromethyl)benzonitrile To a mixture of 4-iodo-2-(trifluoromethyl)benzonitrile (51 g, 171.7 mmol) and $Cu_2O$ (24.5 g, 172 mmol) in DMF (500 mL) was added 5,5-dimethylimidazolidine-2,4-dione (33 g, 255 mmol). The mixture was heated at 150° C. for 12 hours and cooled to room temperature. The reaction mixture was filtered through a pad of Celite. The filtrate was concentrated under reduced pressure to about 50 mL. The residue was poured into ice-water (800 mL) and stirred at room temperature for 30 minutes. To the mixture was added 28% aqueous ammonia solution (60 mL) and the resulting blue suspension was stirred for 0.5 hours. The precipitated solid was collected by filtration and washed with THF (50 mL) to afford 4-(4,4-dimethyl-2,5-dioxoimidazolidin-1-yl)-2-(trifluoromethyl)benzonitrile as a pale white solid (50 g, 98%). LCMS (ESI) m/z: 298 [M+H]$^+$.

Step B. (Z)-4-(3-(4-chlorobut-2-en-1-yl)-4,4-dimethyl-2,5-dioxoimidazolidin-1-yl)-2-(trifluoromethyl)benzonitrile To a mixture of 4-(4,4-dimethyl-2,5-dioxoimidazolidin-1-yl)-2-(trifluoromethyl)benzonitrile (50 g, 168.4 mmol) and $Cs_2CO_3$ (110 g, 336.7 mmol) in $CH_3CN$ (500 mL) at 25° C. was dropped a solution of (Z)-1,4-dichlorobut-2-ene (104 g, 842 mmol) in $CH_3CN$ (200 mL) and heated at 75° C. for 2 hours. The reaction mixture was cooled to room temperature and filtered. The cake was washed with $CH_3CN$ (50 mL). The filtrate was concentrated under reduced pressure. The residue was purified by silica gel chromatography using EtOAc/petroleum ether (1:10) as eluting solvents to afford (Z)-4-(3-(4-chlorobut-2-en-1-yl)-4,4-dimethyl-2,5-dioxoimidazolidin-1-yl)-2-(trifluoromethyl)benzonitrile as a white solid (39 g, 60%). LCMS (ESI) m/z: 386 [M+H]$^+$.

Step C. 4-(1H-pyrazol-4-yl)-2-(trifluoromethyl)benzonitrile

A mixture of 4-(4,4,5,5-tetramethyl-1,3,2-dioxaborolan-2-yl)-1H-pyrazole (CAS: 269410-08-4, Sigma-Aldrich) (300 mg, 1.55 mmol), 4-iodo-2-(trifluoromethyl)benzonitrile (300 mg, 1.01 mmol), $Pd(PPh_3)_4$ (18.6 mg, 0.016 mmol), $K_2CO_3$ (891 mg, 6.46 mmol), and water (2 mL) in 1,4-dioxane (10 mL) under nitrogen was heated at 90° C. overnight. The reaction mixture was concentrated under reduced pressure. The residue was purified by silica gel chromatography using petroleum ether:EtOAc (1:1) as eluting solvents to afford 4-(1H-pyrazol-4-yl)-2-(trifluoromethyl)benzonitrile as a white solid (203 mg, 84%). LCMS (ESI) m/z: 238.1 [M+H]$^1$.

Step D. (Z)-4-(3-(4-(4-(4-cyano-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile A mixture of 4-(1H-pyrazol-4-yl)-2-(trifluoromethyl)benzonitrile (110 mg, 0.46 mmol), (Z)-4-(3-(4-chlorobut-2-en-1-yl)-4,4-dimethyl-2,5-dioxoimidazolidin-1-yl)-2-(trifluoromethyl)benzonitrile (177 mg, 0.46 mmol), and $K_2CO_3$ (127 mg, 0.92 mmol) in DMF (3 mL) was stirred at 60° C. overnight. The reaction mixture was diluted with EtOAc (20 mL), washed with $H_2O$ (20 mL×3), and concentrated under reduced pressure. The residue was purified by silica gel chromatography using petroleum ether:EtOAc (2:1) as eluting solvents to afford (Z)-4-(3-(4-(4-(4-cyano-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile as a white solid (54.6 mg, 20.3%). $^1$H NMR (500 MHz, CDCl$_3$) δ (ppm) 8.15 (d, J=2.0 Hz, 1H), 8.01 (dd, J=8.0 and 2.0 Hz, 1H), 7.94-7.92 (m, 2H), 7.88 (s, 1H), 7.81-7.79 (m, 2H), 7.72 (dd, J=8.5 and 1.5 Hz, 1H), 5.96-5.91 (m, 1H), 5.80-5.75 (m, 1H), 5.04 (d, J=6.5 Hz, 2H), 4.19 (d, J=6.5 Hz, 2H), 1.59 (s, 6H); LCMS (ESI) m/z: 587.2 [M+H]$^1$.

Example 2

(Z)-4-(1-(4-(5,5-dimethyl-3-(4-(methylsulfonyl)-3-(trifluoromethyl)phenyl)-2,4-dioxoimidazolidin-1-yl)but-2-en-1-yl)-1H-pyrazol-4-yl)-2-(trifluoromethyl)benzonitrile Step A.
(4-bromo-2-(trifluoromethyl)phenyl)(methyl)sulfane A mixture of 4-bromo-1-fluoro-2-(trifluoromethyl)benzene (5.81 g, 23.9 mmol) and sodium methanethiolate (25% aqueous solution, 9.7 mL, 31.1 mmol) in DMF (20 mL) was stirred at 50° C. for 2 hours. The reaction mixture was cooled to room temperature, water (120 mL) was added and the resulting mixture was extracted with EtOAc (50 mL×3). The extracts were combined, washed with brine (50 mL×2), dried over magnesium sulfate, filtered, and concentrated under reduced pressure to afford (4-bromo-2-(trifluoromethyl)phenyl)(methyl)sulfane as a yellow oil (6.09 g, 94%), which was used in the next step without further purification.

Step B. 4-bromo-1-(methylsulfonyl)-2-(trifluoromethyl)benzene

A mixture of (4-bromo-2-(trifluoromethyl)phenyl)(methyl)sulfane (5 g, 18.4 mmol) and oxone (33.7 g, 55.2 mmol) in MeOH/H$_2$O (50 mL/50 mL) was stirred at 40° C. overnight. The reaction mixture was concentrated under reduced pressure to remove MeOH. The resulting aqueous mixture was extracted with EtOAc (40 mL×3). The extracts were combined, washed with brine (50 mL), dried over magnesium sulfate, filtered and concentrated under reduced pressure. The residue was purified by silica gel chromatography using petroleum ether:EtOAc (3:2) as eluting solvents to afford 4-bromo-1-(methylsulfonyl)-2-(trifluoromethyl)benzene as a white solid (4.35 g, 78%), which was used for the next step without further purification. LCMS (ESI) m/z: 303.0 [M+H]$^+$.

Step C. 5,5-dimethyl-3-(4-(methylsulfonyl)-3-(trifluoromethyl)phenyl)imidazolidine-2,4-dione A mixture of 4-bromo-1-(methylsulfonyl)-2-(trifluoromethyl)benzene (3.03 g, 10 mmol), 5,5-dimethyl imidazolidine-2,4-dione (1.41 g, 11 mmol), and Cu$_2$O (1.76 g, 12.3 mmol) in DMF (8 mL) was heated at 145° C. overnight. The reaction mixture was cooled to room temperature and filtered. The filtrate was poured into water (50 mL) and extracted with EtOAc (25 mL×3). The extracts were combined, washed with brine (50 mL), dried over magnesium sulfate, filtered, and concentrated under reduced pressure to afford 5,5-dimethyl-3-(4-(methylsulfonyl)-3-(trifluoromethyl)phenyl)imidazolidine-2,4-dione as a pale white solid (2.92 g, 83%), which was used for the next step without further purification. LCMS (ESI) m/z: 351.1 [M+H]$^+$.

Step D. (Z)-1-(4-chlorobut-2-en-1-yl)-5,5-dimethyl-3-(4-(methylsulfonyl)-3-(trifluoromethyl)phenyl)imidazolidine-2,4-dione A mixture of 5,5-dimethyl-3-(4-(methylsulfonyl)-3-(trifluoromethyl)phenyl)imidazolidine-2,4-dione (2.1 g, 6.0 mmol), (Z)-1,4-dichlorobut-2-ene (3.72 g, 30 mmol), and Cs$_2$CO$_3$ (2.93 g, 9.0 mmol) in MeCN (10 mL) was heated at 80° C. for 3 hours. After the mixture was cooled to room temperature, water (30 mL) was added and the resulting mixture was extracted with EtOAc (30 mL×3). The extracts were combined, washed with brine (50 mL×2), dried over magnesium sulfate, filtered and concentrated under reduced pressure. The residue was purified by silica gel chromatography using petroleum ether:EtOAc (1:1) as eluting solvents to afford (Z)-1-(4-chlorobut-2-en-1-yl)-5,5-dimethyl-3-(4-(methylsulfonyl)-3-(trifluoromethyl)phenyl)imidazolidine-2,4-dione as a yellow solid. (1.87 g, 71%). LCMS (ESI) m/z: 439.1 [M+H]$^+$.

Step E. (Z)-4-(1-(4-(5,5-dimethyl-3-(4-(methylsulfonyl)-3-(trifluoromethyl)phenyl)-2,4-dioxoimidazolidin-1-yl)but-2-en-1-yl)-1H-pyrazol-4-1-2-trifluoromethyl)benzonitrile A mixture of (Z)-1-(4-chlorobut-2-en-1-yl)-5,5-dimethyl-3-(4-(methylsulfonyl)-3-(trifluoromethyl)phenyl)imidazolidine-2,4-dione (370 mg, 0.86 mmol), 4-(1H-pyrazol-4-yl)-2-(trifluoromethyl)benzonitrile [Ex1, step C] (200 mg, 0.86 mmol), and K$_2$CO$_3$ (360 mg, 2.58 mmol) in DMF (2 mL) was heated at 60° C. overnight. The reaction mixture was concentrated under reduced pressure. The residue was purified by preparative HPLC to afford (Z)-4-(1-(4-(5,5-dimethyl-3-(4-(methylsulfonyl)-3-(trifluoromethyl)phenyl)-2,4-dioxoimidazolidin-1-yl)but-2-en-1-yl)-1H-pyrazol-4-yl)-2-(trifluoromethyl)benzonitrile as a white solid (100 mg, 19%). $^1$H NMR (500 MHz, DMSO-d$_6$) δ (ppm) 8.62 (s, 1H), 8.37 (d, J=9 Hz, 1H), 8.23 (m, 2H), 8.16 (s, 1H), 8.12 (m, 3H), 5.78 (m, 2H), 5.03 (d, J=6 Hz, 2H), 4.24 (d, J=5.5 Hz, 2H), 3.35 (s, 3H), 1.51 (s, 6H); LCMS (ESI) m/z: 640.2 [M+H]$^+$.

Example 3

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-1H-pyrazol-1-yl)but-2-en-1-yl)imidazolidine-2,4-dione Step A. 4-(4-(methylsulfonyl)-3-(trifluoromethyl)phenyl)-1H-pyrazole A mixture of 4-(4,4,5,5-tetramethyl-1,3,2-dioxaborolan-2-yl)-1H-pyrazole (300 mg, 1.55 mmol), 4-bromo-1-(methylsulfonyl)-2-(trifluoromethyl)benzene (300 mg, 0.99 mmol), Pd(PPh$_3$)$_4$ (18.6 mg, 0.016 mmol), K$_2$CO$_3$ (891 g, 6.46 mmol), and water (2 mL) in 1,4-dioxane (10 mL) under nitrogen was heated at 90° C. overnight. The reaction mixture was concentrated under reduced pressure. The residue was purified by silica gel chromatography using petroleum ether:EtOAc (1:1) as eluting solvents to afford 4-(4-(methylsulfonyl)-3-(trifluoromethyl)phenyl)-1H-pyrazole as white powder (190 mg, 66%). LCMS (ESI) m/z: 291.1 [M+H]$^+$.

Step B. (Z)-5,5-dimethyl-3-(4-(methylsulfonyl)-3-(trifluoromethyl)phenyl)-1-(4-(4-(4-(methylsulfonyl)-3-(trifluoromethyl)phenyl)-1H-pyrazol-1-yl)but-2-en-1-yl)imidazolidine-2,4-dione A mixture of 4-(4-(methylsulfonyl)-3-(trifluoromethyl)phenyl)-1H-pyrazole (190 mg, 0.66 mmol), (Z)-1-(4-chlorobut-2-en-1-yl)-5,5-dimethyl-3-(4-(methylsulfonyl)-3-(trifluoromethyl)-phenyl)imidazolidine-2,4-dione (289 mg, 0.66 mmol), and K$_2$CO$_3$ (360 mg, 2.58 mmol) in DMF (2 mL) was heated at 60° C. overnight. The reaction mixture was concentrated under reduced pressure. The residue was purified by preparative HPLC to afford (Z)-5,5-dimethyl-3-(4-(methylsulfonyl)-3-(trifluoromethyl)phenyl)-1-(4-(4-(4-(methylsulfonyl)-3-(trifluoromethyl)phenyl)-1H-pyrazol-1-yl)but-2-en-1-yl)imidazolidine-2,4-dione as a white solid (60 mg, 13%). $^1$H NMR (500 MHz, DMSO-d$_6$) δ (ppm) 8.62 (d, J=3.5 Hz, 1H), 8.38-8.35 (m, 1H), 8.23-8.10 (m, 6H), 5.81-5.75 (m, 2H), 5.02 (br, 2H), 4.24 (br, 2H), 3.35 (s, 3H), 3.29 (s, 3H), 1.52 (s, 6H); LCMS (ESI) m/z: 693.1 [M+H]$^+$.

Example 4

(Z)-5-(4,4-dimethyl-3-(4-(4-(methylsulfonyl)-3-(trifluoromethyl)phenyl)-1H-pyrazol-1-yl)but-2-en-1-yl)-2,5-dioxoimidazolidin-1-yl)-3-(trifluoromethyl)picolinonitrile Step A. 5-iodo-3-(triftuoromethyl)pyridin-2-ol A mixture of 3-(trifluoromethyl)pyridin-2-ol (3.0 g, 18.5 mmol) and N-iodosuccinimide (4.2 g, 18.5 mmol) in CH$_3$CN (25 mL) and DMF (25 mL) was heated at 80° C. for 2 hours. After the reaction mixture was cooled to room temperature, water was added and the resulting mixture was extracted with EtOAc (70 mL×2). The extracts were combined, washed with brine (120 mL×3), dried over sodium sulfate, filtered, and concentrated under reduced pressure to afford 5-iodo-3-(trifluoromethyl)pyridin-2-ol as a yellow solid (4.0 g, 74%). $^1$H NMR (500 MHz, CDCl$_3$) δ (ppm) 13.37 (bs, 1H), 7.98 (d, J=2.0 Hz, 1H), 7.85 (d, J=2.0 Hz, 1H); LCMS (ESI) m/z: 290 [M+H]$^+$.

Step B. 2-chloro-5-iodo-3-(trifluoromethyl)pyridine

A suspension of 5-iodo-3-(trifluoromethyl)pyridin-2-ol (3.0 g, 10.4 mmol) in POCl$_3$ (8 mL) was heated at 100° C. overnight. After cooling down to room temperature, the mixture was poured into ice (50 g). The resulting aqueous layer was neutralized by Na$_2$CO$_3$ and extracted with EtOAc (70 mL×2). The extracts were combined, dried over sodium sulfate, filtered, and concentrated under reduced pressure. The residue was purified by silica gel chromatography using petroleum ether:EtOAc (100:1~4:1) as eluting solvents to afford 2-chloro-5-iodo-3-(trifluoromethyl)pyridine as a white solid (2.0 g, 63%). $^1$H NMR (500 MHz, CDCl$_3$) δ (ppm) 8.78 (d, J=2.0 Hz, 1H), 8.28 (d, J=2.0 Hz, 1H).

Step C. 3-(6-chloro-5-(trifluoromethyl)pyridin-3-yl)-5,5-dimethylimidazolidine-2,4-dione To a mixture of 2-chloro-5-iodo-3-(trifluoromethyl)pyridine (1.4 g, 4.5 mmol) in DMF (10 mL) was added 5,5-dimethylimidazolidine-2,4-dione (637 mg, 5.0 mmol) and Cu$_2$O (1.6 g, 11.4 mmol) and heated at 150° C. overnight. The reaction mixture was cooled to room temperature and filtered. The filtrate was poured into water (70 mL), 28% aqueous ammonia solution (6 mL) was added, and the resulting mixture was extracted with EtOAc (70 mL×2). The extracts were combined, washed with brine (100 mL×3), dried over sodium sulfate, filtered, and concentrated under reduced pressure. The residue was purified by silica gel chromatography using petroleum ether:EtOAc (10:1~1:1) as eluting solvents to afford 3-(6-chloro-5-(trifluoromethyl)pyridin-3-yl)-5,5-dimethylimidazolidine-2,4-dione as a white solid (955 mg, 68%). LCMS (ESI) m/z: 308 [M+H]$^1$.

Step D. 5-(4,4-dimethyl-2,5-dioxoimidazolidin-1-yl)-3-(trifluoromethyl)picolinonitrile To a solution of 3-(6-chloro-5-(trifluoromethyl)pyridin-3-yl)-5,5-dimethylimidazolidine-2,4-dione (950 mg, 3.1 mmol) in DMF (15 mL) was added Zn(CN)$_2$ (434 mg, 3.7 mmol), Pd$_2$(dba)$_3$ (283 mg, 0.31 mmol), and dppf (343 mg, 0.62 mmol). The mixture under N$_2$ atmosphere was heated at 140° C. overnight. After the reaction mixture was cooled to room temperature and filtered, the filtrate was extracted with EtOAc (70 mL×2). The extracts were combined, washed with brine (100 mL×3), dried over sodium sulfate, filtered, and concentrated under reduced pressure. The residue was purified by silica gel chromatography using petroleum ether:EtOAc (4:1~1:1) as eluting solvents to afford 5-(4,4-dimethyl-2,5-dioxoimidazolidin-1-yl)-3-(trifluoromethyl)picolinonitrile as a brown solid (910 mg, 99%). LCMS (ESI) m/z: 299 [M+H]$^+$.

Step E. (Z)-5-(3-(4-chlorobut-2-en-1-yl)-4,4-dimethyl-2,5-dioxoimidazolidin-1-yl)-3-(trifluoromethyl)picolinonitrile To a mixture of 5-(4,4-dimethyl-2,5-dioxoimidazolidin-1-yl)-3-(trifluoromethyl)picolinonitrile (1.1 g, 3.65 mmol) and Cs$_2$CO$_3$ (2.4 g, 7.3 mmol) in CH$_3$CN (20 mL) at 25° C. was dropped a solution of (Z)-1,4-dichlorobut-2-ene (2.28 g, 18.3 mmol) in CH$_3$CN (2 mL) and heated at 75° C. for 2 hours. The reaction mixture was cooled down to room temperature, filtered, and washed with CH$_3$CN. The filtrate was concentrated under reduced pressure. The residue was purified by silica gel chromatography using petroleum ether: EtOAc (10:1~4:1) as eluting solvents to afford (Z)-5-(3-(4-Chlorobut-2-en-1-yl)-4,4-dimethyl-2,5-dioxoimidazolidin-1-yl)-3-(trifluoromethyl)picolinonitrile as a light yellow solid (780 mg, 56%). LCMS (ESI) m/z: 387 [M+H]$^+$.

Step F. (Z)-5-(4,4-dimethyl-3-(4-(4-(4-(methylsulfonyl)-3-(trifluoromethyl)phenyl)-1H-pyrazol-1-yl) but-2-en-1-yl)-2, 5-dioxoimidazolidin-1-yl)-3-(trifluoromethyl)picolinonitrile A mixture of (Z)-5-(3-(4-chlorobut-2-en-1-yl)-4,4-dimethyl-2,5-dioxoimidazolidin-1-yl)-3-(trifluoromethyl)picolinonitrile (100 mg, 0.34 mmol), 4-(4-(methylsulfonyl)-3-(trifluoromethyl)phenyl)-1H-pyrazole (160 mg, 0.41 mmol), and K$_2$CO$_3$ (140 mg, 0.90 mmol) in DMF (5 mL) was stirred at 60° C. for 2 hours. The reaction mixture was filtered and the filtrate was concentrated under reduced pressure. The residue was purified by preparative HPLC to afford (Z)-5-(4,4-dimethyl-3-(4-(4-(4-(methylsulfonyl)-3-(trifluoromethyl)phenyl)-1H-pyrazol-1-yl)but-2-enyl)-2,5-dioxoimidazolidin-1-yl)-3-(trifluoromethyl)picolinonitrile as a white solid (160 mg, 20%). $^1$H NMR (500 MHz, DMSO-d$_6$) δ (ppm) 9.22 (s, 1H), 8.65 (s, 1H), 8.62 (s, 1H), 8.23 (s, 1H), 8.14-8.18 (m, 3H), 5.73-5.83 (m, 2H), 5.03 (d, J=6.5 Hz, 2H), 4.26 (d, J=6.5 Hz, 2H), 3.29 (s, 3H), 1.52 (s, 6H); LCMS (ESI) m/z: 641.2 [M+H]$^+$.

Example 5

(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile Step A. (4-bromo-2-chlorophenyl)(methyl)sulfane A mixture of 4-bromo-2-chloro-1-fluorobenzene (5 g, 23.9 mmol) and sodium methanethiolate (25% aqueous solution, 9.7 mL, 31.1 mmol) in DMF (20 mL) was stirred at 50° C. for 2 hours. The reaction mixture was cooled to room temperature, water (120 mL) was added, and the resulting mixture was extracted with EtOAc (50 mL×3). The extracts were combined, washed with brine (50 mL×2), dried over magnesium sulfate, filtered, and concentrated under reduced pressure to afford (4-bromo-2-chlorophenyl)(methyl)sulfane as a yellow oil (5.2 g, 92%), which was used in the next step without further purification.

Step B. 4-bromo-2-chloro-1-(methylsulfonyl)benzene

A mixture of (4-bromo-2-chlorophenyl)(methyl)sulfane (5 g, 21.3 mmol) and oxone (39 g, 63.8 mmol) in MeOH/H$_2$O (50 mL/50 mL) was stirred at 40° C. overnight. The reaction mixture was concentrated under reduced pressure to remove MeOH. The resulting aqueous mixture was extracted with EtOAc (40 mL×3). The extracts were combined, washed with brine (50 mL), dried over magnesium sulfate, filtered, and concentrated under reduced pressure. The residue was purified by silica gel chromatography using petroleum ether:EtOAc (3:1) as eluting solvents to afford 4-bromo-2-chloro-1-(methylsulfonyl)benzene as a white solid (3 g, 52.6%), which was used for the next step without further purification. LCMS (ESI) m/z: 270.0 [M+H]+.

Step C. 4-(3-chloro-4-(methylsulfonyl)phenyl)-1H-pyrazole

A mixture of 4-bromo-2-chloro-1-(methylsulfonyl)benzene (1.5 g, 5.60 mmol), 4-(4,4,5,5-tetramethyl-1,3,2-dioxaborolan-2-yl)-1H-pyrazole (1.6 g, 8.40 mmol), Pd(dppf)$_2$Cl$_2$ (100 mg, 0.14 mmol), and K$_2$CO$_3$ (2.30 g, 16.79 mmol) in toluene (8 mL), EtOH (8 mL), and H$_2$O (4 mL) was heated at 100° C. under nitrogen for 12 hours. The reaction mixture was quenched with water and extracted by EtOAc (150 mL×2). The extracts were combined, washed with brine, dried over sodium sulfate, filtered, and concentrated under reduced pressure. The residue was purified by silica gel chromatography using petroleum ether:EtOAc (1:1~3:1) as eluting solvents to afford 4-(3-chloro-4-(methylsulfonyl)phenyl)-1H-pyrazole as a yellow solid (700 mg, 49%). LCMS (ESI) m/z: 257.1 [M+H]+.

Step D. (Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile A mixture of (Z)-5-(4-chlorobut-2-en-1-yl)-4,4-dimethyl-2,5-dioxoimidazolidin-1-yl-3-(trifluoromethyl)picolinonitrile (180 mg, 0.47 mmol), K$_2$CO$_3$ (160 mg, 0.12 mmol), and 4-(3-chloro-4-(methylsulfonyl)phenyl)-1H-pyrazole (100 mg, 0.39 mmol) in DMF (5 mL) was heated at 60° C. for 2 hours. The reaction mixture was filtered and concentrated under reduced pressure. The residue was purified by preparative HPLC to afford (Z)-5-(3-(4-(4-(3-chloro-4-(methylsulfonyl)phenyl)-1H-pyrazol-1-yl)but-2-en-1-yl)-4,4-dimethyl-2,5 dioxoimidazolidin-1-yl)-3-(trifluoromethyl)picolinonitrile as a white solid (70 mg, 75%). $^1$H NMR (500 MHz, DMSO-d$_6$) δ (ppm) 9.22 (s, 1H), 8.65 (s, 1H), 8.52 (s, 1H), 8.16 (s, 1H), 7.98 (d, J=9.0 Hz, 2H), 7.81 (d, J=10.0 Hz, 1H), 5.82-5.73 (m, 2H), 5.02 (d, J=6.5 Hz, 2H), 4.25 (d, J=6.5 Hz, 2H), 3.36 (s, 3H), 1.52 (s, 6H); MS (ESI) m/z: 607.2 [M+H]+.

Example 6

(Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile Step A. 4,4,5,5-tetramethyl-2-(4-(methylsulfonyl)-3-(trifluoromethyl)phenyl)-1,3,2-dioxaborolane A mixture of 4-bromo-1-(methylsulfonyl)-2-(trifluoromethyl)benzene (2 g, 6.6 mmol), 4,4,4',4',5,5,5',5'-octamethyl-2,2'-bi(1,3,2-dioxaborolane) (1.68 g, 6.6 mmol), potassium acetate (1.94 g, 19.8 mmol), and Pd(dppf)$_2$Cl$_2$ (50 mg) in 1,4-dioxane (15 mL) was stirred at 95° C. for 3 hours. The reaction mixture was filtered and the filtrate was concentrated under reduced pressure. The residue was purified by silica gel chromatography using EtOAc:petroleum ether (1:4) as eluting solvents to afford 4,4,5,5-tetramethyl-2-(4-(methylsulfonyl)-3-(trifluoromethyl)phenyl)-1,3,2-dioxaborolane as a white solid (1.6 g, 69%). LCMS (ESI) m/z: 291.0 [M−82+Na]+.

Step B. (Z)-4-(3-(4-(4-bromo-3,5-dimethyl-1H-pyrazol-1-yl)but-2-en-1-yl)-4,4-dimethyl-2,5-dioxoimidazolidin-1-yl)-2-(trifluoromethyl)benzonitrile To a solution of 4-bromo-3,5-dimethyl-1H-pyrazole (CAS: 3398-16-1, Sigma-Aldrich) (300 mg, 1.71 mmol) in DMF (6 mL) at 0° C. was added sodium hydride (60% in mineral oil, 89 mg). After stirring for 30 minutes, a solution of (Z)-4-(3-(4-chlorobut-2-enyl)-4,4-dimethyl-2,5-dioxoimidazolidin-1-yl)-2-(trifluoromethyl)benzonitrile (660 mg, 1.71 mmol) in DMF (2 mL) was added and the mixture was stirred at room temperature overnight. The reaction mixture was quenched with water (20 mL) and extracted with EtOAc (20 mL×3). The extracts were combined, washed with brine, dried over sodium sulfate, filtered, and concentrated under reduced pressure. The residue was purified by preparative TLC (EtOAc:petroleum ether, 1:1) to afford (Z)-4-(3-(4-(4-bromo-3,5-dimethyl-1H-pyrazol-1-yl)but-2-en-1-yl)-4,4-dimethyl-2,5-dioxoimidazolidin-1-yl)-2-(trifluoromethyl)benzonitrile as a white solid (500 mg, 56%). LCMS (ESI) m/z: 524.2 [M+H]+.

Step C. (Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile A mixture of (Z)-4-(3-(4-(4-bromo-3,5-dimethyl-1H-pyrazol-1-yl)but-2-en-1-yl)-4,4-dimethyl-2,5-dioxoimidazolidin-1-yl)-2-(trifluoromethyl)benzonitrile (100 mg, 0.19 mmol), 4,4,5,5-tetramethyl-2-(4-(methylsulfonyl)-3-(trifluoromethyl)phenyl)-1,3,2-dioxaborolane (67 mg, 0.19 mmol), potassium phosphate (121 mg, 0.57 mmol), and Pd(PPh$_3$)$_4$ (15 mg) in DMF (4 mL) was stirred at 110° C. for 40 hours. The reaction mixture was filtered and the filtrate was concentrated under reduced pressure. The residue was purified by preparative HPLC to afford (Z)-4-(3-(4-(3,5-dimethyl-4-(4-(methylsulfonyl)-3-(trifluoromethyl)phenyl)-1H-pyrazol-1-yl)but-2-en-1-yl)-4,4-dimethyl-2,5-dioxoimidazolidin-1-yl)-2-(trifluoromethyl)benzonitrile as a white solid (20 mg, 16%). $^1$H NMR (500 MHz, CDCl$_3$) δ (ppm) 8.33 (d, J=8.0 Hz, 1H), 8.15 (d, J=1.5 Hz, 1H), 8.00 (dd, J=8.5 and 1.5 Hz, 1H), 7.92 (d, J=8.5 Hz, 1H), 7.76 (s, 1H), 7.61 (dd, J=8.0 and 1.5 Hz, 1H), 5.82 (m, 1H), 5.72 (m, 1H), 4.90 (d, J=6.5 Hz, 2H), 4.20 (d, J=7.0 Hz, 2H), 3.23 (s, 3H), 2.33 (s, 3H), 2.28 (s, 3H), 1.59 (s, 6H); LCMS (ESI) m/z: 668.1 [M+H]+.

Example 7

(Z)-4-(3-(4-(5,5-dimethyl-3-(4-(methylsulfonyl)-3-(trifluoromethyl)phenyl)-2-oxoimidazolidin-1-yl)but-2-en-1-yl)-4,4-dimethyl-2,5-dioxoimidazolidin-1-yl)-2-(trifluoromethyl)benzonitrile Step A. 2-methyl-N1-(4-(methylsulfonyl)-3-(trifluoromethyl)phenyl)propane-1,2-diamine A mixture of 4-bromo-1-(methylsulfonyl)-2-(trifluoromethyl)benzene (600 mg, 2.0 mmol), 2-methylpropane-1,2-diamine (262 mg, 3.0 mmol), and potassium carbonate (552 mg, 4.0 mmol) in DMF (5 mL) was heated at 60° C. overnight. The reaction mixture was quenched with water (20 mL) and extracted with EtOAc (10 mL×3). The extracts were combined, washed with brine, dried over sodium sulfate, filtered, and concentrated under reduced pressure to afford 2-methyl-N1-(4-(methylsulfonyl)-3-(trifluoromethyl)phenyl)

phenyl)propane-1,2-diamine as a brown oil (400 mg, 65%). LCMS (ESI) m/z: 311.1 [M+H]⁺.

Step B. (Z)-4-(4,4-dimethyl-3-(4-((2-methyl-1-((4-(methylsulfonyl)-3-(trifluoromethyl)phenyl)amino) propan-2-yl)amino)but-2-en-1-yl)-2,5-dioxoimidazolidin-1-yl)-2-(trifluoromethyl)benzonitrile A mixture of 2-methyl-N1-(4-(methylsulfonyl)-3-(trifluoromethyl)phenyl)propane-1,2-diamine (400 mg, 1.3 mmol), (Z)-4-(3-(4-chlorobut-2-en-1-yl)-4,4-dimethyl-2,5-dioxoimidazolidin-1-yl)-2-(trifluoromethyl)benzonitrile (500 mg, 1.3 mmol), and potassium carbonate (538 mg, 3.9 mmol) in DMF (5 mL) was stirred at room temperature for 12 hours. The reaction mixture was purified by silica gel chromatography using MeOH:DCM (1:10) as eluting solvents to afford (Z)-4-(4,4-dimethyl-3-(4-((2-methyl-1-((4-(methylsulfonyl)-3-(trifluoromethyl)phenyl)amino)propan-2-yl)amino)but-2-en-1-yl)-2,5-dioxoimidazolidin-1-yl)-2-(trifluoromethyl)benzonitrile as a yellow solid (150 mg, 18%). LCMS (ESI) m/z: 660.2 [M+H]⁺.

Step C. (Z)-4-(3-(4-(5,5-dimethyl-3-(4-(methylsulfonyl)-3-(trifluoromethyl)phenyl)-2-oxoimidazolidin-1-yl)but-2-en-1-yl)-4,4-dimethyl-2,5-dioxoimidazolidin-1-yl)-2-(trifluoromethyl)benzonitrile A mixture of (Z)-4-(4,4-dimethyl-3-(4-((2-methyl-1-((4-(methylsulfonyl)-3-(trifluoromethyl)phenyl)amino)propan-2-yl)amino)but-2-en-1-yl)-2,5-dioxoimidazolidin-1-yl)-2-(trifluoromethyl)benzonitrile (150 mg, 0.23 mmol), CDI (50 mg, 0.30 mmol), and potassium carbonate (83 mg, 0.60 mmol) in DMF (5 mL) was heated at 50° C. overnight. The reaction mixture was quenched with water (10 mL) and extracted with EtOAc (10 mL×3). The extracts were combined, washed with brine, dried over sodium sulfate, filtered, and concentrated under reduced pressure. The residue was purified by silica gel chromatography using EtOAc:petroleum ether (2:1) as eluting solvents to afford (Z)-4-(3-(4-(5,5-dimethyl-3-(4-(methylsulfonyl)-3-(trifluoromethyl)phenyl)-2-oxoimidazolidin-1-yl)but-2-en-1-yl)-4,4-dimethyl-2,5-dioxoimidazolidin-1-yl)-2-(trifluoromethyl)benzonitrile as a white solid (45 mg, 29%). ¹H NMR (500 MHz, DMSO-d₆) δ (ppm) 8.50 (d, J=2 Hz, 1H), 8.34 (d, J=8.5 Hz, 1H), 8.21 (d, J=2 Hz, 1H), 8.15 (d, J=8.5 Hz, 1H), 8.06 (dd, J=1.5 and 8 Hz, 1H), 7.77 (dd, J=2 and 9.5 Hz, 1H), 5.54 (m, 2H), 4.23 (d, J=4.5 Hz, 2H), 4.01 (d, J=4.5 Hz, 2H), 3.75 (s, 2H), 3.34 (s, 3H), 1.50 (s, 6H), 1.35 (s, 6H); LCMS (ESI) m/z: 686.2 [M+H]⁺.

Example 8

(Z)-3-(3-chloro-4-(methylsulfonyl)phenyl)-1-(4-(5,5-dimethyl-3-(4-(methylsulfonyl)-3-(trifluoromethyl)phenyl)-2-oxoimidazolidin-1-yl)but-2-en-1-yl)-5,5-dimethylimidazolidine-2,4-dione Step A. 3-(3-chloro-4-(methylsulfonyl)phenyl)-5,5-dimethylimidazolidine-2,4-dione A mixture of 4-bromo-2-chloro-1-(methylsulfonyl)benzene (3 g, 11.2 mmol), 5,5-dimethyl imidazolidine-2,4-dione (1.72 g, 13.4 mmol), and Cu₂O (1.76 g, 12.3 mmol) in DMF (8 mL) was heated at 145° C. overnight. The reaction mixture was cooled to room temperature and filtered. The filtrate was poured into water (50 mL) and extracted with EtOAc (25 mL×3). The extracts were combined, washed with brine (50 mL), dried over magnesium sulfate, filtered, and concentrated under reduced pressure to afford 3-(3-chloro-4-(methylsulfonyl)phenyl)-5,5-dimethylimidazolidine-2,4-dione as a white solid (2.65 g, 75%), which was used for the next step without further purification. LCMS (ESI) m/z: 317.0 [M+H]⁺.

Step B. (Z)-3-(3-chloro-4-(methylsulfonyl)phenyl)-1-(4-chlorobut-2-en-1-yl)-5,5-dimethylimidazolidine-2,4-dione A mixture of 3-(3-chloro-4-(methylsulfonyl)phenyl)-5,5-dimethylimidazolidine-2,4-dione (2 g, 6.33 mmol), (Z)-1,4-dichlorobut-2-ene (3.92 g, 31.6 mmol), and cesium carbonate (3.09 g, 9.49 mmol) in MeCN (10 mL) was heated at 80° C. for 3 hours. After the mixture was cooled to room temperature, water (30 mL) was added and the resulting mixture was extracted with EtOAc (30 mL×3). The extracts were combined, washed with brine (50 mL×2), dried over magnesium sulfate, filtered, and concentrated under reduced pressure. The residue was purified by silica gel chromatography using petroleum ether: EtOAc (1:1) as eluting solvents to afford (Z)-3-(3-chloro-4-(methylsulfonyl)phenyl)-1-(4-chlorobut-2-en-1-yl)-5,5-dimethyl imidazolidine-2,4-dione as a white solid (1.66 g, 65%). LCMS (ESI) m/z: 405.0 [M+H]⁺.

Step C. (Z)-3-(3-chloro-4-(methylsulfonyl)phenyl)-5,5-dimethyl-1-(4-((2-methyl-1-((4-(methylsulfonyl)-3-(trifluoromethyl)phenyl)amino)propan-2-yl) amino)but-2-en-1-yl)imidazolidine-2,4-dione A mixture of 2-methyl-N1-(4-(methylsulfonyl)-3-(trifluoromethyl)phenyl)propane-1,2-diamine (200 mg, 0.65 mmol), (Z)-3-(3-chloro-4-(methylsulfonyl)phenyl)-1-(4-chlorobut-2-en-1-yl)-5,5-dimethylimidazolidine-2,4-dione (261 mg, 0.65 mmol), and K₂CO₃ (178 mg, 1.29 mmol) in DMF (3 mL) was stirred at 60° C. overnight. The reaction mixture was poured into water (15 mL) and extracted with ethyl acetate (15 mL×2). The extracts were combined, washed with brine (15 mL), dried over sodium sulfate, filtered, and concentrated under reduced pressure. The residue was purified by silica gel chromatography using ethyl acetate as the eluting solvent to afford (Z)-3-(3-chloro-4-(methylsulfonyl)phenyl)-5,5-dimethyl-1-(4-((2-methyl-1-((4-(methylsulfonyl)-3-(trifluoromethyl)phenyl)amino)propan-2-yl)-amino)but-2-en-1-yl)imidazolidine-2,4-dione as a yellow solid (270 mg, 62%). LCMS (ESI) m/z: 679.1 [M+H]⁺.

Step D. (Z)-3-(3-chloro-4-(methylsulfonyl)phenyl)-1-(4-(5,5-dimethyl-3-(4-(methylsulfonyl)-3-(trifluoromethyl)phenyl)-2-oxoimidazolidin-1-yl)but-2-en-1-yl)-5,5-dimethylimidazolidine-2,4-dione To a mixture of (Z)-3-(3-chloro-4-(methylsulfonyl)phenyl)-5,5-dimethyl-1-(4-((2-methyl-1-((4-(methylsulfonyl)-3-(trifluoromethyl)phenyl)amino)propan-2-yl)-amino)but-2-en-1-yl)imidazolidine-2,4-dione (200 mg, 0.29 mmol) and triethylamine (88 mg, 0.87 mmol) in THF (5 mL) at room temperature was added bis(trichloromethyl)carbonate (173 mg, 0.59 mmol). The mixture was stirred at room temperature for 5 hours. The reaction mixture was poured into water (15 mL) and extracted with ethyl acetate (15 mL×2). The extracts were combined, washed with brine, dried over sodium sulfate, filtered, and concentrated under reduced pressure. The residue was purified by preparative HPLC to afford (Z)-3-(3-chloro-4-(methylsulfonyl)phenyl)-1-(4-(5,5-dimethyl-3-(4-(methylsulfonyl)-3-(trifluoromethyl)phenyl)-2-oxoimidazolidin-1-yl)but-2-en-1-yl)-5,5-dimethylimidazolidine-2,4-dione as a brown solid (24 mg, 11%). $^1$H NMR (500 MHz, CDCl$_3$) δ (ppm) 8.27 (s, 1H), 8.23 (s, 1H), 8.21 (s, 1H), 7.89 (s, 1H), 7.75 (d, J=2.0 Hz, 1H), 7.74 (d, J=2.0 Hz, 1H), 5.60-5.61 (m, 2H), 4.28 (d, J=4.9 Hz, 2H), 4.05 (d, J=5.2 Hz, 2H), 3.66 (s, 2H), 3.27 (s, 3H), 3.16 (s, 3H), 1.58 (s, 6H), 1.45 (s, 6H); LCMS (ESI) m/z: 705.0 [M+H]$^+$.

Example 9

(Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2-oxoimidazolidin-1-yl)-2-(trifluoromethyl)benzonitrile Step A. 4-((2-amino-2-methylpropyl)amino)-2-(trifluoromethyl)benzonitrile A mixture of 4-fluoro-2-(trifluoromethyl)benzonitrile (3.0 g, 15.87 mmol), 2-methylpropane-1,2-diamine (2.1 g, 23.85 mmol), and K$_2$CO$_3$ (4.5 g, 29.61 mmol) in DMF (30 mL) was stirred at 80° C. for 3 hours. The reaction mixture was poured into water (90 mL) and extracted with ethyl acetate (60 mL×4). The extracts were combined, washed with brine (50 mL×2), dried over sodium sulfate, filtered and concentrated under reduced pressure to afford 4-((2-amino-2-methylpropyl)amino)-2-(trifluoromethyl)benzonitrile as a white solid (2.94 g, 72%). LCMS (ESI) m/z: 258.0 [M+H]$^+$.

Step B. (Z)-4-((2-((4-(5,5-dimethyl-3-(4-(methylsulfonyl)-3-trifluoromethyl)phenyl)-2,4-dioxoimidazolidin-1-yl)but-2-en-1-yl)amino)-2-methylpropyl)amino)-2-(trifluoromethyl)benzonitrile A mixture of 4-(2-amino-2-methylpropylamino)-2-(trifluoromethyl)benzonitrile (1.0 g, 3.89 mmol), (Z)-1-(4-chlorobut-2-en-1-yl)-5,5-dimethyl-3-(4-(methylsulfonyl)-3-(trifluoromethyl)phenyl)imidazolidine-2,4-dione (1.7 g, 3.89 mmol), and K$_2$CO$_3$ (1070 mg, 7.78 mmol) in DMF (10 mL) was stirred at 60° C. overnight. The mixture was poured into water (50 mL) and extracted with ethyl acetate (50 mL×3). The extracts were combined, washed with brine (50 mL), dried with sodium sulfate, filtered, and concentrated under reduced pressure to afford (Z)-4-((2-((4-(5,5-dimethyl-3-(4-(methylsulfonyl)-3-(trifluoromethyl)phenyl)-2,4-dioxoimidazolidin-1-yl)but-2-en-1-yl)amino)-2-methylpropyl)amino)-2-(trifluoromethyl)benzonitrile as a brown solid (1.5 g, 59%), which was used for the next step without further purification. MS (ESI) m/z: 660.1 [M+H]$^+$.

Step C. (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2-oxoimidazolidin-1-yl)-2-(trifluoromethyl)benzonitrile A mixture Of (Z)-4-((2-((4-(5,5-dimethyl-3-(4-(methylsulfonyl)-3-(trifluoromethyl)phenyl)-2,4-dioxoimidazolidin-1-yl)but-2-en-1-yl)amino)-2-methylpropyl)amino)-2-(trifluoromethyl)benzonitrile (500 mg, 0.76 mmol), di-tert-butyl dicarbonate (5 mL), and DMAP (50 mg) in dichloromethane (10 mL) was stirred at room temperature overnight. The reaction mixture was poured into water (20 mL) and extracted with dichloromethane (20 mL×2). The extracts were combined, washed with brine (30 mL), dried over sodium sulfate, filtered, and concentrated under reduced pressure. The residue was purified by preparative HPLC to afford (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2-oxoimidazolidin-1-yl)-2-(trifluoromethyl)benzonitrile as a white solid (40 mg, 8%). $^1$HNMR (500 MHz, DMSO-d$_6$) δ (ppm) 8.38 (s, 1H), 8.36 (s, 1H), 8.23 (d, J=1.5 Hz, 1H), 8.08-8.12 (m, 2H), 7.79 (d, J=7.0 Hz, 1H), 5.50-5.59 (m, 2H), 4.22 (d, J=5.2 Hz, 2H), 4.02 (d, J=5.2 Hz, 2H), 3.76 (s, 2H), 3.36 (s, 3H), 1.50 (s, 6H), 1.36 (s, 6H); LCMS (ESI) m/z: 686.1 [M+H]$^+$.

Example 10

(Z)-4-(4,4-dimethyl-3-(4-(3-(4-(methylsulfonyl)-3-(trifluoromethyl)phenyl)-2-oxoimidazolidin-1-yl)but-2-en-1-yl)-2,5-dioxoimidazolidin-1-yl)-2-(trifluoromethyl)benzonitrile Step A. N1-(4-(methylsulfonyl)-3-(trifluoromethyl)phenyl)ethane-1,2-diamine A mixture of 4-bromo-1-(methylsulfonyl)-2-(trifluoromethyl)benzene (1 g, 3.3 mmol), ethane-1,2-diamine (993 mg, 16.6 mmol) and potassium carbonate (1.37 g, 9.9 mmol) in DMF (5 mL) was stirred at 100° C. overnight. The reaction mixture was quenched with water (40 mL) and extracted with EtOAc (40 mL×3). The extracts were combined, washed with brine, dried over sodium sulfate, filtered, and concentrated under reduced pressure to afford N1-(4-(methylsulfonyl)-3-(trifluoromethyl)phenyl)ethane-1,2-diamine as a white solid (700 mg, 75%). LCMS (ESI) m/z: 283.1 [M+H]$^+$.

Step B. (Z)-4-(4,4-dimethyl-3-(4-((2-((4-(methylsulfonyl)-3-(trifluoromethyl)phenyl)amino)ethyl)amino)but-2-en-1-yl)-2,5-dioxoimidazolidin-1-yl)-2-(trifluoromethyl)benzonitrile A mixture of N1-(4-(methylsulfonyl)-3-(trifluoromethyl)phenyl)ethane-1,2-diamine (700 mg, 2.5 mmol), (Z)-4-(3-(4-chlorobut-2-en-1-yl)-4,4-dimethyl-2,5-dioxoimidazolidin-1-yl)-2-(trifluoromethyl)benzonitrile (955 mg, 2.5 mmol), and potassium carbonate (514 mg, 3.7 mmol) in DMF (5 mL) was stirred at room temperature for 2 hours. The reaction mixture was quenched with water (20 mL) and extracted with EtOAc (30 mL×3). The extracts were combined, washed with brine, dried over sodium sulfate, filtered, and concentrated under reduced pressure. The residue was purified by silica gel chromatography using petroleum ether: EtOAc (10%) as eluting solvents to afford (Z)-4-(4,4-dimethyl-3-(4-((2-((4-(methylsulfonyl)-3-(trifluoromethyl)phenyl)amino)ethyl)amino)but-2-en-1-yl)-2,5-dioxoimidazolidin-1-yl)-2-(trifluoromethyl)benzonitrile as a white solid (250 mg, 16%). LCMS (ESI) m/z: 632.2 [M+H]$^+$.

Step C. (Z)-4-(4,4-dimethyl-3-(4-(3-(4-(methylsulfonyl)-3-(trifluoromethyl)phenyl)-2-oxoimidazolidin-1-yl)but-2-en-1-yl)-2,5-dioxoimidazolidin-1-yl)-2-(trifluoromethyl)benzonitrile To a mixture of (Z)-4-(4,4-dimethyl-3-(4-(((2-((4-(methylsulfonyl)-3-(trifluoromethyl)phenyl)amino)ethyl)amino)but-2-en-1-yl)-2,5-dioxoimidazolidin-1-yl)-2-(trifluoromethyl)benzonitrile (80 mg, 0.13 mmol) and triphosgene (49 mg, 0.17 mmol) in THF (3 mL) was added triethylamine (2 drops). The mixture was stirred at room temperature for 2 hours. The reaction mixture was filtered and the filtrate was concentrated under reduced pressure. The residue was purified by preparative HPLC to afford (Z)-4-(4,4-dimethyl-3-(4-(3-(4-(methylsulfonyl)-3-(trifluoromethyl)phenyl)-2-oxoimidazolidin-1-yl)but-2-en-1-yl)-2,5-dioxoimidazolidin-1-yl)-2-(trifluoromethyl)benzonitrile as a white solid (9 mg, 11%). $^1$H NMR (500 MHz, DMSO-$d_6$) δ (ppm) 8.55 (d, J=2.5 Hz, 1H), 8.32 (d, J=10.5 Hz, 1H), 8.20 (d, J=2.0 Hz, 1H), 8.15 (d, J=11.5 Hz, 1H), 8.05 (dd, J=12.5 and 2.0 Hz, 1H), 7.76 (d, J=11.5 and 2.5 Hz, 1H), 5.60-5.69 (m, 2H), 4.18 (d, J=7.5 Hz, 2H), 4.05 (d, J=8.5 Hz, 2H), 3.95 (t, J=10.0 Hz, 2H), 3.56 (t, J=10.0 Hz, 2H), 3.24 (s, 3H), 1.49 (s, 6H); LCMS (ESI) m/z: 658.1 [M+H]$^+$.

Example 11

(Z)-4-(3-(4-(3-(3-chloro-4-(methylsulfonyl)phenyl)-2-oxoimidazolidin-1-yl)but-2-en-1-yl)-4,4-dimethyl-2,5-dioxoimidazolidin-1-yl)-2-(trifluoromethyl)benzonitrile Step A. (Z)-tert-butyl (2-((4-(3-(4-cyano-3-(trifluoromethyl)phenyl)-5,5-dimethyl-2,4-dioxoimidazolidin-1-yl)but-2-en-1-yl)amino)ethyl)carbamate A mixture of tert-butyl 2-aminoethylcarbamate (748 mg, 4.7 mmol), (Z)-4-(3-(4-chlorobut-2-enyl)-4,4-dimethyl-2,5-dioxoimidazolidin-1-yl)-2-(trifluoromethyl)benzonitrile (1.2 g, 3.1 mmol), and potassium carbonate (1.3 g, 9.35 mmol) in DMF (7 mL) was stirred at room temperature overnight. The reaction mixture was quenched with water (40 mL) and extracted with EtOAc (40 mL×3). The extracts were combined, washed with brine, dried over sodium sulfate, filtered, and concentrated under reduced pressure. The residue was purified by silica gel chromatography using EtOAc:MeOH (20:1) as eluting solvents to afford (Z)-tert-butyl (2-((4-(3-(4-cyano-3-(trifluoromethyl)phenyl)-5,5-dimethyl-2,4-dioxoimidazolidin-1-yl)but-2-en-1-yl)amino)ethyl)carbamate as a white solid (800 mg, 50%). LCMS (ESI) m/z: 510.2 [M+H]$^+$.

Step B. (Z)-tert-butyl 3-(4-(3-(4-cyano-3-(trifluoromethyl)phenyl)-5,5-dimethyl-2,4-dioxoimidazolidin-1-yl)but-2-en-1-yl)-2-oxoimidazolidine-1-carboxylate A mixture of (Z)-tert-butyl (2-((4-(3-(4-cyano-3-(trifluoromethyl)phenyl)-5,5-dimethyl-2,4-dioxoimidazolidin-1-yl)but-2-en-1-yl)amino)ethyl)carbamate (500 mg, 0.98 mmol), CDI (198 mg, 1.18 mmol), and potassium carbonate (406 mg, 2.95 mmol) in DMF (5 mL) was stirred at 50° C. overnight. The reaction mixture was quenched with water (30 mL) and extracted with EtOAc (25 mL×3). The extracts were combined, washed with water (15 mL), dried over sodium sulfate, filtered, and concentrated under reduced pressure. The residue was purified by silica gel chromatography using EtOAc:petroleum ether (1:1) as eluting solvents to afford (Z)-tert-butyl 3-(4-(3-(4-cyano-3-(trifluoromethyl)phenyl)-5,5-dimethyl-2,4-dioxoimidazolidin-1-yl)but-2-en-1-yl)-2-oxoimidazolidine-1-carboxylate as a white solid (420 mg, 80%). LCMS (ESI) m/z: 480.1 [M−56+1]$^+$.

Step C. (Z)-4-(4,4-dimethyl-2,5-dioxo-3-(4-(2-oxoimidazolidin-1-yl)but-2-en-1-yl)imidazolidin-1-yl)-2-(trifluoromethyl)benzonitrile A solution of (Z)-tert-butyl 3-(4-(3-(4-cyano-3-(trifluoromethyl)phenyl)-5,5-dimethyl-2,4-dioxoimidazolidin-1-yl)but-2-en-1-yl)-2-oxoimidazolidine-1-carboxylate (400 mg, 0.75 mmol) and TFA (1 mL) in dichloromethane (4 mL) was stirred at room temperature for 2 hours. To the reaction mixture was added dichloromethane, washed with an aqueous NaHCO$_3$ solution (15 mL) and water (15 mL), dried over sodium sulfate, filtered, and concentrated under reduced pressure to afford (Z)-4-(4,4-dimethyl-2,5-dioxo-3-(4-(2-oxoimidazolidin-1-yl)but-2-en-1-yl)imidazolidin-1-yl)-2-(trifluoromethyl)benzonitrile as a white solid (250 mg, 76%). LCMS (ESI) m/z: 436.1 [M+H]$^+$.

Step D. (Z)-4-(3-(4-(3-(3-chloro-4-(methylsulfonyl)phenyl)-2-oxoimidazolidin-1-yl)but-2-en-1-yl)-4,4-dimethyl-2,5-dioxoimidazolidin-1-yl)-2-(trifluoromethyl)benzonitrile A mixture of (Z)-4-(4,4-dimethyl-2,5-dioxo-3-(4-(2-oxoimidazolidin-1-yl)but-2-en-1-yl)imidazolidin-1-yl)-2-(trifluoromethyl)benzonitrile (150 mg, 0.34 mmol), 4-bromo-2-chloro-1-(methylsulfonyl)benzene (93 mg, 0.34 mmol), cesium carbonate (337 mg, 1.03 mmol), Pd$_2$(dba)$_3$ (20 mg), and Xantphos (40 mg) in toluene (5 mL) was stirred at 95° C. overnight. The reaction mixture was poured into water (20 mL) and extracted with EtOAc (20 mL×3). The extracts were combined, washed with brine, dried over sodium sulfate, filtered, and concentrated under reduced pressure. The residue was purified by preparative HPLC to afford (Z)-4-(3-(4-(3-(3-chloro-4-(methylsulfonyl)phenyl)-2-oxoimidazolidin-1-yl)but-2-en-1-yl)-4,4-dimethyl-2,5-dioxoimidazolidin-1-yl)-2-(trifluoromethyl)benzonitrile as a white solid (21 mg, 10%). $^1$H NMR (500 MHz, DMSO-$d_6$) δ (ppm) 8.33 (d, J=8.5 Hz, 1H), 8.20 (d, J=1.5 Hz, 1H), 8.04-8.06 (m, 2H), 7.95 (d, J=9.0 Hz, 1H), 7.65 (d, J=9.0 and 2.0 Hz, 1H), 5.68-5.70 (m, 1H), 5.58-5.59 (m, 1H), 4.17 (d, J=6.0 Hz, 2H), 4.04 (d, J=7.0 Hz, 2H), 3.90 (t, J=8.0 Hz, 2H), 3.53 (t, J=8.0 Hz, 2H), 3.31 (s, 3H), 1.49 (s, 6H). LCMS (ESI) m/z: 624.1 [M+H]$^+$.

Example 12

(Z)-4-(1-(4-(3-(4-cyano-3-(trifluoromethyl)phenyl)-5,5-dimethyl-2,4-dioxoimidazolidin-1-yl)but-2-en-1-yl)pyrrolidin-3-yl)-2-(trifluoromethyl)benzonitrile Step A. tert-butyl 4-(((trifluoromethyl)sulfonyl)oxy)-2,3-dihydro-1H-pyrrole-1-carboxylate and tert-butyl 3-(((trifluoromethyl)sulfonyl)oxy)-2,5-dihydro-1H-pyrrole-1-carboxylate To a solution of tert-butyl 3-oxopyrrolidine-1-carboxylate (5 g, 27 mmol) in THF (50 mL) at −78° C. was added a solution of LiHMDS in THF (1.0 M, 29 mL, 29 mmol). After stirring for 20 minutes, a solution of Tf$_2$NPh (11.5 g, 32 mmol) in THF (20 mL) was added dropwise. The mixture was stirred at room temperature for 1 hour and quenched with water (100 mL). The organic layer was separated, dried over magnesium sulfate, filtered, and concentrated under reduced pressure. The residue was purified by silica gel chromatography using petroleum ether as eluting solvent to afford a mixture of tert-butyl 4-(((trifluoromethyl)sulfonyl)oxy)-2,3-dihydro-1H-pyrrole-1-carboxylate and tert-butyl 3-(((trifluoromethyl)sulfonyl)oxy)-2,5-dihydro-1H-pyrrole-1-carboxylate as a white solid (3 g, 36%). LCMS (ESI) m/z: 262.0 [M−56+H]$^+$.

Step B. tert-butyl 4-(4,4,5,5-tetramethyl-1,3,2-dioxaborolan-2-yl)-2,3-dihydro-1H-pyrrole-1-carboxylate and tert-butyl 3-(4,4,5,5-tetramethyl-1,3,2-dioxaborolan-2-yl)-2,5-dihydro-1H-pyrrole-1-carboxylate A mixture of tert-butyl 4-(((trifluoromethyl)sulfonyl)oxy)-2,3-dihydro-1H-pyrrole-1-carboxylate and tert-butyl 3-(((trifluoromethyl)sulfonyl)oxy)-2,5-dihydro-1H-pyrrole-1-carboxylate (1 g, 3.15 mmol), 4,4,4',4',5,5,5',5'-octamethyl-2,2'-bi(1,3,2-dioxaborolane) (880 mg, 3.47 mmol), potassium acetate (927 mg, 9.46 mmol), Pd(dppf)$_2$Cl$_2$ (100 mg), and dppf (75 mg) in 1,4-dioxane (10 mL) was stirred at 80° C. overnight. The reaction mixture was concentrated under reduced pressure. The residue was partitioned with water (10 mL) and EtOAc (20 mL). The organic layer was separated, washed with brine (10 mL), dried over magnesium sulfate, filtered and concentrated under reduced pressure. The residue was purified by silica gel chromatography using petroleum ether as eluting solvent to afford a mixture of tert-butyl 4-(4,4,5,5-tetramethyl-1,3,2-dioxaborolan-2-yl)-2,3-dihydro-1H-pyrrole-1-carboxylate and tert-butyl 3-(4,4,5,5-tetramethyl-1,3,2-dioxaborolan-2-yl)-2,5-dihydro-1H-pyrrole-1-carboxylate as a white solid (800 mg, 86%). LCMS (ESI) m/z: 240.2 [M−56+H]$^+$.

Step C. tert-butyl 4-(4-cyano-3-(trifluoromethyl)phenyl)-2,3-dihydro-1H-pyrrole-1-carboxylate and tert-butyl 3-(4-cyano-3-(trifluoromethyl)phenyl)-2,5-dihydro-1H-pyrrole-1-carboxylate A mixture of tert-butyl 4-(4,4,5,5-tetramethyl-1,3,2-dioxaborolan-2-yl)-2,3-dihydro-1H-pyrrole-1-carboxylate and tert-butyl 3-(4,4,5,5-tetramethyl-1,3,2-dioxaborolan-2-yl)-2,5-dihydro-1H-pyrrole-1-carboxylate (770 mg, 2.61 mmol), 4-iodo-2-(trifluoromethyl)benzonitrile (775 mg, 2.61 mmol), potassium carbonate (1.08 g, 7.83 mmol), and Pd(PPh$_3$)$_4$ (100 mg, 0.09 mmol) in 1,4-dioxane (5 mL) was stirred at 90° C. overnight. The reaction mixture was concentrated under reduced pressure. The residue was purified by silica gel chromatography using EtOAc:petroleum ether (1:10) as eluting solvents to afford a mixture of tert-butyl 4-(4-cyano-3-(trifluoromethyl)phenyl)-2,3-dihydro-1H-pyrrole-1-carboxylate and tert-butyl 3-(4-cyano-3-(trifluoromethyl)phenyl)-2,5-dihydro-1H-pyrrole-1-carboxylate as a white solid (400 mg, 45%), which was used in the next step without further purification. LCMS (ESI) m/z: 283.1 [M−56+H]$^+$.

Step D. tert-butyl 3-(4-cyano-3-(trifluoromethyl)phenyl)pyrrolidine-1-carboxylate A suspension of tert-butyl 4-(4-cyano-3-(trifluoromethyl)phenyl)-2,3-dihydro-1H-pyrrole-1-carboxylate and tert-butyl 3-(4-cyano-3-(trifluoromethyl)phenyl)-2,5-dihydro-1H-pyrrole-1-carboxylate (370 mg, 1.10 mmol) and Pd/C (100 mg) in THF (8 mL) was stirred under hydrogen at room temperature for 2 hours. The reaction mixture was filtered and the filtrate was concentrated to afford tert-butyl 3-(4-cyano-3-(trifluoromethyl)phenyl)pyrrolidine-1-carboxylate as a white powder (350 mg, 94%), which was used for the next step without further purification. LCMS (ESI) m/z: 285.1 [M−56+H]$^+$.

Step E. 4-(pyrrolidin-3-yl)-2-(trifluoromethyl)benzonitrile

To a solution of tert-butyl 3-(4-cyano-3-(trifluoromethyl)phenyl)pyrrolidine-1-carboxylate (340 mg, 1.0 mmol) in 1,4-dioxane (2 mL) was added a solution of HCl in 1,4-dioxane (4.0 M, 2 mL) and stirred at room temperature for 2 hours. The reaction mixture was concentrated under reduced pressure to afford 4-(pyrrolidin-3-yl)-2-(trifluoromethyl)benzonitrile hydrochloride as a white solid (350 mg, 94%), which was used for the next step without further purification. LCMS (ESI) m/z: 241.0 [M+H]$^+$.

Step F. (Z)-4-(1-(4-(3-(4-cyano-3-(trifluoromethyl)phenyl)-5,5-dimethyl-2,4-dioxoimidazolidin-1-yl)but-2-en-1-yl)pyrrolidin-3-yl)-2-(trifluoromethyl)benzonitrile A mixture of 4-(pyrrolidin-3-yl)-2-(trifluoromethyl)benzonitrile hydrochloride (160 mg, 0.67 mmol), (Z)-4-(3-(4-chlorobut-2-en-1-yl)-4,4-dimethyl-2,5-dioxoimidazolidin-1-yl)-2-(trifluoromethyl)-benzonitrile (256 mg, 0.67 mmol), and potassium carbonate (138 mg, 1 mmol) in DMF (3 mL) was stirred at 60° C. for 4 hours. The reaction mixture was filtered and the filtrate was concentrated under reduced pressure. The residue was purified by preparative HPLC to afford (Z)-4-(1-(4-(3-(4-cyano-3-(trifluoromethyl)phenyl)-5,5-dimethyl-2,4-dioxoimidazolidin-1-yl)but-2-en-1-yl)pyrrolidin-3-yl)-2-(trifluoromethyl)benzonitrile as a white solid (31 mg, 7.9%). $^1$H NMR (500 MHz, DMSO-d$_6$) δ (ppm) 8.32 (d, J=8.5 Hz, 1H), 8.19 (d, J=1.5 Hz, 1H), 8.10 (d, J=8.5 Hz, 1H), 8.04 (dd, J=8.5 and 1.5 Hz, 1H), 7.92 (s, 1H), 7.84 (d, J=8 Hz, 1H), 5.68 (m, 1H), 5.56 (m, 1H), 4.10 (d, J=6 Hz, 2H), 3.55 (m, 1H), 3.28 (d, J=6.5 Hz, 2H), 2.85-2.87 (m, 2H), 2.59-2.66 (m, 2H), 2.32-2.34 (m, 1H), 1.75 (m, 1H), 1.47 (s, 6H); LCMS (ESI) m/z: 590.3 [M+H]$^+$.

Example 13

(Z)-4-(4,4-dimethyl-3-(4-(4-(4-(methylsulfonyl)-3-(trifluoromethyl)phenyl)-2-oxopyrrolidin-1-yl)but-2-en-1-yl)-2,5-dioxoimidazolidin-1-yl)-2-(trifluoromethyl)benzonitrile

Step A. (E)-ethyl 3-(4-(methylsulfonyl)-3-(trifluoromethyl)phenyl)acrylate

A solution of 4-bromo-1-(methylsulfonyl)-2-(trifluoromethyl)benzene (3 g, 9.9 mmol) and ethyl acrylate (1.29 g, 12.87 mmol), KOAc (1.457 g, 14.85 mmol), and Pd(OAc)$_2$ (50 mg) in DMF (30 mL) under nitrogen was stirred at 120° C. for 5 hours. The reaction mixture was quenched with water (50 mL) and extracted with EtOAc (50 mL×3). The extracts were combined, washed with water (15 mL), dried over sodium sulfate, filtered, and concentrated under reduced pressure. The residue was purified by silica gel chromatography using EtOAc:petroleum ether (1:1) as eluting solvents to afford (E)-ethyl 3-(4-(methylsulfonyl)-3-(trifluoromethyl)phenyl)acrylate as white solid (3.1 g, 97.2%). LCMS (ESI) m/z: 323.0 [M+H]$^+$.

Step B. ethyl 3-(4-(methylsulfonyl)-3-(trifluoromethyl)phenyl)-4-nitrobutanoate To a solution of (E)-ethyl 3-(4-(methylsulfonyl)-3-(trifluoromethyl)phenyl)acrylate (2 g, 6.21 mmol) in CH$_3$NO$_2$ (10 mL) at 0° C. was added dropwise DBU (0.78 g, 6.21 mmol) and stirred at room temperature for 3 hours. The reaction mixture was concentrated under reduced pressure. The residue was purified by silica gel chromatography using petroleum ether: EtOAc (1:2) as eluting solvents to afford ethyl 3-(4-(methylsulfonyl)-3-(trifluoromethyl)phenyl)-4-nitrobutanoate as a yellow solid (1.5 g, 63%). LCMS (ESI) m/z: 406.0 [M+Na]⁺.

Step C. 4-(4-(methylsulfonyl)-3-(trifluoromethyl)phenyl)pyrrolidin-2-one

To a solution of ethyl 3-(4-(methylsulfonyl)-3-(trifluoromethyl)phenyl)-4-nitrobutanoate (1.3 g, 3.391 mmol) in AcOH (20 mL) at 8° C. was added Fe powder (1.89 g, 33.9 mmol). The mixture was stirred at 120° C. for 3 hours. The reaction mixture was quenched with 1 N solution of HCl (20 mL) and extracted with ethyl acetate (50 mL×2). The extracts were combined, washed with water (20 mL), dried over sodium sulfate, filtered, and concentrated under reduced pressure. The residue was purified by silica gel chromatography using DCM:methanol (20:1) as eluting solvents to afford 4-(4-(methylsulfonyl)-3-(trifluoromethyl)phenyl)pyrrolidin-2-one as a white solid (1 g, 95.9%). LCMS (ESI) m/z: 308.0 [M+H]⁺.

Step D. (Z)-1-(4-chlorobut-2-en-1-yl)-4-(4-(methylsulfonyl)-3-(trifluoromethyl)phenyl)pyrrolidin-2-one To a solution of 4-(4-methanesulfonyl-3-(trifluoromethyl)phenyl)pyrrolidin-2-one (2 g, 6.51 mmol) in THF (20 mL) at 0° C. was added NaH (60% in mineral oil, 1.04 g, 26 mmol). After the mixture was stirred at 0° C. for 40 minutes, (Z)-1,4-dichlorobut-2-ene (4 0.07 g, 32.54 mmol) was added. The mixture was stirred at room temperature for 16 hours and concentrated under reduced pressure. The residue was purified by silica gel chromatography using petroleum ether:EtOAc (1:1) as eluting solvents to afford (Z)-1-(4-chlorobut-2-en-1-yl)-4-(4-(methylsulfonyl)-3-(trifluoromethyl)phenyl)pyrrolidin-2-one as a white solid (1.7 g, 66%). LCMS (ESI) m/z: 396.0. [M+H]⁺.

Step E. (Z)-4-(4,4-dimethyl-3-(4-(4-(4-(methylsulfonyl)-3-(trifluoromethyl)phenyl)-2-oxopyrrolidin-1-yl)but-2-en-1-yl)-2,5-dioxoimidazolidin-1-yl)-2-(trifluoromethyl)benzonitrile A mixture of (Z)-1-(4-chlorobut-2-en-1-yl)-4-(4-(methylsulfonyl)-3-(trifluoromethyl)phenyl)pyrrolidin-2-one (40 mg, 0.10 mmol), 4-(4,4-dimethyl-2,5-dioxoimidazolidin-1-yl)-2-(trifluoromethyl)benzonitrile (30 mg, 0.10 mmol), and Cs₂CO₃ (66 mg, 0.20 mmol) in DMF (1 mL) was heated at 70° C. for 1.5 hours. The reaction mixture was filtered and the filtrate was concentrated under reduced pressure. The residue was purified by preparative HPLC to afford (Z)-4-(4,4-dimethyl-3-(4-(4-(4-(methylsulfonyl)-3-(trifluoromethyl)phenyl)-2-oxopyrrolidin-1-yl)but-2-en-1-yl)-2,5-dioxoimidazolidin-1-yl)-2-(trifluoromethyl)benzonitrile as a white solid (20 mg, 30.1%). ¹H NMR (500 MHz, CDCl₃) δ (ppm) 8.28 (d, J=8.2 Hz, 1H), 8.00 (s, 1H), 7.99 (dd, J=1.7 and 8.44 Hz, 1H), 7.92 (d, J=8.4 Hz, 1H), 7.74 (s, 1H), 7.65 (d, J=8.1 Hz, 1H), 5.60-5.74 (m, 2H), 4.07-4.24 (m, 4H), 3.91 (t, J=9.6 Hz, 1H), 3.72-3.80 (m, 1H), 3.49 (dd, J=6.3 and 9.9 Hz, 1H), 3.19 (s, 3H), 2.96 (dd, J=17.0 and =7.5 Hz, 1H), 2.57 (dd, J=17.0 and 7.5 Hz, 1H), 1.57 (s, 6H); LCMS (ESI) m/z: 657.1 [M+H]⁺.

Example 14

(Z)-4-(3-(4-(4-(3-chloro-4-(methylsulfonyl)phenyl)-2-oxopyrrolidin-1-yl)but-2-en-1-yl)-4,4-dimethyl-2,5-dioxoimidazolidin-1-yl)-2-(trifluoromethyl)benzonitrile Step A. (E)-ethyl 3-(3-chloro-4-(methylsulfonyl)phenyl)acrylate A solution of 4-bromo-2-chloro-1-(methylsulfonyl)benzene (3 g, 11.1 mmol), ethyl acrylate (1.45 g, 14.47 mmol), KOAc (1.64 g, 16.70 mmol), and Pd(OAc)₂ (125 mg, 0.556 mmol) in DMF (50 mL) under nitrogen was stirred at 120° C. for 5 hours. The reaction mixture was quenched with water (150 mL) and extracted with EtOAc (50 mL×2). The extracts were combined, washed with water (15 mL×2), dried over sodium sulfate, filtered, and concentrated under reduced pressure. The residue was purified by silica gel chromatography using EtOAc:petroleum ether (1:2) as eluting solvents to afford (E)-ethyl 3-(3-chloro-4-(methylsulfonyl)phenyl)acrylate as a white solid (3.2 g, 99.6%). LCMS (ESI) m/z: 289.0 [M+H]⁺.

Step B. ethyl 3-(3-chloro-4-(methylsulfonyl)phenyl)-4-nitrobutanoate

To a solution of (E)-ethyl 3-(3-chloro-4-(methylsulfonyl)phenyl)acrylate (3 g, 10.39 mmol) in CH₃NO₂ (15 mL) at 0° C. was added dropwise DBU (1.58 g, 10.39 mmol) and stirred at room temperature for 3 hours. The reaction mixture was concentrated under reduced pressure. The residue was purified by silica gel chromatography using petroleum ether:EtOAc (1:2) as eluting solvents to afford ethyl 3-(3-chloro-4-(methylsulfonyl)phenyl)-4-nitrobutanoate as a yellow solid (2.2 g, 60.53%). LCMS (ESI) m/z: 350.1 [M+H]⁺.

Step C. 4-(3-chloro-4-(methylsulfonyl)phenyl)pyrrolidin-2-one

To a solution of ethyl 3-(3-chloro-4-(methylsulfonyl)phenyl)-4-nitrobutanoate (2 g, 5.717 mmol) in AcOH (20 mL) at 8° C. was added Fe powder (3.2 g, 57.17 mmol). The mixture was stirred at 120° C. for 3 hours. The reaction mixture was quenched with 1 N solution of HCl (20 mL) and extracted with ethyl acetate (50 mL×2). The extracts were combined, washed with water (20 mL), dried over sodium sulfate, filtered, and concentrated under reduced pressure. The residue was purified by silica gel chromatography using DCM:methanol (20:1) as eluting solvents to afford 4-(3-chloro-4-(methylsulfonyl)phenyl)pyrrolidin-2-one as a white solid (1.3 g, 83.06%). LCMS (ESI) m/z: 274.1 [M+H]⁺.

Step D. (Z)-4-(3-chloro-4-(methylsulfonyl)phenyl)-1-(4-chlorobut-2-en-1-yl)pyrrolidin-2-one To a solution of 4-(3-chloro-4-(methylsulfonyl)phenyl)pyrrolidin-2-one (1.2 g, 2.75 mmol) in THF (20 mL) at 0° C. was added NaH (60% in mineral oil, 0.703 g, 17.58 mmol). After the mixture was stirred at 0° C. for 40 minutes, (Z)-1,4-dichlorobut-2-ene (2.75 g, 21.98 mmol) was added. The mixture was stirred at room temperature for 16 hours and concentrated under reduced pressure. The residue was purified by silica gel chromatography using petroleum ether:EtOAc (3:1) as eluting solvents to afford (Z)-4-(3-chloro- 4-(methylsulfonyl)phenyl)-1-(4-chlorobut-2-en-1-yl)pyrrolidin-2-one as a colorless oil (0.6 g, 45.33%). LCMS (ESI) m/z: 362.0 [M+H]$^+$.

Step E. (Z)-4-(3-(4-(4-(3-chloro-4-(methylsulfonyl)phenyl)-2-oxopyrrolidin-1-yl)but-2-en-1-yl)-4,4-dimethyl-2,5-dioxoimidazolidin-1-yl)-2-(trifluoromethyl)benzonitrile A solution of (Z)-4-(3-chloro-4-(methylsulfonyl)phenyl)-1-(4-chlorobut-2-en-1-yl)pyrrolidin-2-one (120 mg, 0.33 mmol), 4-(4,4-dimethyl-2,5-dioxoimidazolidin-1-yl)-2-(trifluoromethyl)benzonitrile (98.5 mg, 0.331 mmol), and Cs$_2$CO$_3$ (216 mg, 0.66 mmol) in DMF (1 mL) was heated at 70° C. for 1.5 hours. The reaction mixture was filtered and the filtrate was concentrated under reduced pressure. The residue was purified by preparative HPLC to afford (Z)-4-(3-(4-(4-(3-chloro-4-(methylsulfonyl)phenyl)-2-oxopyrrolidin-1-yl)but-2-en-1-yl)-4,4-dimethyl-2,5-dioxoimidazolidin-1-yl)-2-(trifluoromethyl)benzonitrile as a white solid (107 mg, 51.84%). $^1$H NMR (500 MHz, CDCl$_3$) δ (ppm) 8.13 (s, 1H), 8.11 (d, J=8.2 Hz, 1H), 7.99 (dd, J=1.6 and 8.4 Hz, 1H), 7.92 (d, J=8.4 Hz, 1H), 7.73 (s, 1H), 7.33 (d, J=8.1 Hz, 1H), 5.60-5.74 (m, 2H), 4.08-4.24 (m, 4H), 3.86 (t, J=9.5 Hz, 1H), 3.62-3.70 (m, 1H), 3.46 (dd, J=6.3 and 9.8 Hz, 1H), 3.27 (s, 3H), 2.92 (dd, J=9.2 and 16.9 Hz, 1H), 2.56 (dd, J=7.4 and 16.9 Hz, 1H), 1.57 (s, 6H); LCMS (ESI) m/z: 623.1 [M+H]$^+$.

Example 15

(Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione Step A. (Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione A mixture of 5,5-dimethyl-3-(4-(methylsulfonyl)-3-(trifluoromethyl)phenyl)imidazolidine-2,4-dione (153 mg, 0.435 mmol), (Z)-1-(4-chlorobut-2-en-1-yl)-4-(4-(methylsulfonyl)-3-(trifluoromethyl)phenyl)pyrrolidin-2-one (172 mg, 0.435 mmol), and Cs$_2$CO$_3$ (284 mg, 0.871 mmol) in DMF (2 mL) was stirred at 70° C. for 1.5 hours. The mixture was filtered and the filtrate was concentrated under reduced pressure. The residue was purified by preparative HPLC to afford (Z)-5,5-dimethyl-3-(4-(methylsulfonyl)-3-(trifluoromethyl)phenyl)-1-(4-(4-(4-(methylsulfonyl)-3-(trifluoromethyl)phenyl)-2-oxopyrrolidin-1-yl)but-2-en-1-yl)imidazolidine-2,4-dione as a white solid (5 mg, 2%). $^1$H NMR (500 MHz, CD$_3$OD) δ (ppm) 8.39 (d, J=8.7 Hz, 1H), 8.26-8.28 (m, 2H), 8.12 (d, J=8.6 Hz, 1H), 7.93 (s, 1H), 7.87 (d, J=8.8 Hz, 1H), 5.77-5.82 (m, 1H), 5.65-5.70 (m, 1H), 4.21-4.25 (m, 4H), 3.96-4.00 (m, 2H), 3.59-3.63 (m, 1H), 3.26 (s, 3H), 3.22 (s, 3H), 2.92-2.97 (m, 1H), 2.2.61-2.66 (m, 1H), 1.59 (s, 6H); LCMS (ESI) m/z: 710.2 [M+H]$^+$.

Example 16

(Z)-4-(1-(4-(3-(3-chloro-4-(methylsulfonyl)phenyl)-5,5-dimethyl-2,4-dioxoimidazolidin-1-yl)but-2-en-1-yl)-3-hydroxypyrrolidin-3-yl)-2-(trifluoromethyl)benzonitrile Step A. tert-butyl 3-(4-cyano-3-(trifluoromethyl)phenyl)-3-hydroxypyrrolidine-1-carboxylate To a mixture of 4-iodo-2-(trifluoromethyl)benzonitrile (946 mg, 2.702 mmol) in THF (5 mL) at 0° C. was added a solution of BuLi in hexane (1.29 mL, 3.25 mmol) and stirred under nitrogen for 1 hour. To the mixture at 0° C. was added a solution of tert-butyl 3-oxopyrrolidine-1-carboxylate (500 mg, 2.702 mmol) in THF (5 mL) and stirred at room temperature for 4 hours. The reaction mixture was quenched with H$_2$O (20 mL) and extracted with ethyl acetate (20 mL×2). The extracts were combined, washed with brine (20 mL), dried over sodium sulfate, filtered, and concentrated under reduced pressure to afford tert-butyl 3-(4-cyano-3-(trifluoromethyl)phenyl)-3-hydroxypyrrolidine-1-carboxylate as a white solid (368 mg, 38%). LCMS (ESI) m/z: 301.0 [M−56+H]$^+$.

Step B. 4-(3-hydroxypyrrolidin-3-yl)-2-(trifluoromethyl)benzonitrile

To a solution of tert-butyl 3-(4-cyano-3-(trifluoromethyl)phenyl)-3-hydroxypyrrolidine-1-carboxylate (368 mg, 1.03 mmol) in dichloromethane (4 mL) at −20° C. was added TFA (4 mL) and stirred at room temperature overnight. The reaction mixture was diluted with dichloromethane (20 mL), washed with an aqueous solution of NaHCO$_3$ (20 mL) and water (20 mL), dried over sodium sulfate, filtered, and concentrated under reduced pressure to afford 4-(3-hydroxypyrrolidin-3-yl)-2-(trifluoromethyl)benzonitrile as a white solid (258 mg, 97%). LCMS (ESI) m/z: 257.0 [M+H]$^+$.

Step C. (Z)-4-(1-(4-(3-(3-chloro-4-(methylsulfonyl)phenyl)-5,5-dimethyl-2,4-dioxoimidazolidin-1-yl)but-2-en-1-yl)-3-hydroxypyrrolidin-3-yl)-2-(trifluoromethyl)benzonitrile A mixture of 4-(3-hydroxypyrrolidin-3-yl)-2-(trifluoromethyl)benzonitrile (150 mg, 0.586 mmol), 3-(3-chloro-4-(methylsulfonyl)phenyl)-1-((Z)-4-chlorobut-2-en-1-yl)-5,5-dimethylimidazolidine-2,4-dione (260 mg, 0.644 mmol), and K$_2$CO$_3$ (162 mg, 1.172 mmol) in DMF (4.0 mL) was stirred at room temperature overnight. The reaction mixture was filtered and the filtrate was concentrated. The residue was purified by preparative HPLC to afford (Z)-4-(1-(4-(3-(3-chloro-4-(methylsulfonyl)phenyl)-5,5-dimethyl-2,4-dioxo imidazolidin-1-yl)but-2-en-1-yl)-3-hydroxypyrrolidin-3-yl)-2-(trifluoromethyl)benzonitrile as a white solid (14 mg, 4%). $^1$HNMR (500 MHz, CDCl$_3$) δ (ppm) 8.29 (s, 1H), 8.15 (t, J=8.0 Hz, 2H), 8.08 (s, 1H), 8.00 (d, J=8.0 Hz, 1H), 7.90 (s, 1H), 7.75 (d, J=7.5 Hz, 1H), 5.58-5.65 (m, 2H), 4.09 (d, J=4.7 Hz, 2H), 3.41 (s, 3H), 3.30 (d, J=6.2 Hz, 2H), 2.96-3.02 (m, 2H), 2.69-2.76 (m, 2H), 2.10-2.11 (m, 2H), 1.46 (s, 6H); LCMS (ESI) m/z: 625.1 [M+H]$^+$.

Example 17

(Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile Step A. (Z)-4-(3-(4-(2-aminoethyl)amino)but-2-en-1-yl)-4,4-dimethyl-2,5-dioxoimidazolidin-1-yl)-2-(trifluoromethyl)benzonitrile A solution of (Z)-tert-butyl 2-((4-(3-(4-cyano-3-(trifluoromethyl)phenyl)-5,5-dimethyl-2,4-dioxoimidazolidin-1-yl)but-2-en-1-yl)amino)ethylcarbamate (700 mg, 1.37 mmol) and TFA (2 mL) in dichloromethane (8 mL) was stirred at room temperature for 2 hours. The reaction mixture was quenched with a saturated NaHCO$_3$ solution (30 mL) and extracted with dichloromethane. The extracts were combined, dried over sodium sulfate, filtered, and concentrated under reduced pressure to afford (Z)-4-(3-(4-((2-aminoethyl)amino)but-2-en-1-yl)-4,4-dimethyl-2,5-dioxoimidazolidin-1-yl)-2-(trifluoromethyl)benzonitrile as a white solid (400 mg, 71%). LCMS (ESI) m/z: 410.2 [M+H]$^+$.

Step B. (Z)-4-(3-(4-(4-(1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile A mixture of (Z)-4-(3-(4-((2-aminoethyl)amino)but-2-en-1-yl)-4,4-dimethyl-2,5-dioxoimidazolidin-1-yl)-2-(trifluoromethyl)benzonitrile (300 mg, 0.73 mmol) and sulfuric diamide (141 mg, 1.47 mmol) in pyridine (5 mL) was stirred at 100° C. overnight. The reaction mixture was concentrated under reduced pressure. The residue was purified by preparative TLC (EtOAc) to afford (Z)-4-(3-(4-(1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile as a white solid (60 mg, 17%). LCMS (ESI) m/z: 472.1 [M+H]$^+$.

Step C. (Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile A mixture of (Z)-4-(3-(4-(1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile (60 mg, 0.13 mmol), 4-bromo-2-chloro-1-(methylsulfonyl)benzene (35 mg, 0.14 mmol), cesium carbonate (124 mg, 0.38 mmol), Pd$_2$(dba)$_3$ (10 mg), and xantphos (20 mg) in toluene (3 mL) was stirred at 95° C. overnight. The reaction mixture was quenched with water (15 mL) and extracted with EtOAc (15 mL×3). The extracts were combined, washed with brine (30 mL), dried over sodium sulfate, filtered, and concentrated under reduced pressure. The residue was purified by preparative HPLC to afford (Z)-4-(3-(4-(5-(3-chloro-4-(methylsulfonyl)phenyl)-1,1-dioxido-1,2,5-thiadiazolidin-2-yl)but-2-en-1-yl)-4,4-dimethyl-2,5-dioxoimidazolidin-1-yl)-2-(trifluoromethyl)benzonitrile as a white solid (9 mg, 11%). $^1$H NMR (500 MHz, CDCl$_3$) δ (ppm) 8.12-8.14 (m, 2H), 7.98 (dd, J=8.5 and 2.0 Hz, 1H), 7.92 (d, J=9 Hz, 1H), 7.34 (d, J=2.5 Hz, 1H), 7.21 (ds, J=9.0 and 2.5 Hz, 1H), 5.76-5.80 (m, 2H), 4.13 (d, J=6.5 Hz, 2H), 3.98 (d, J=6.5 Hz, 2H), 3.90 (t, J=6.5 Hz, 2H), 3.65 (t, J=6.5 Hz, 2H), 3.25 (s, 3H), 1.57 (s, 6H); LCMS (ESI) m/z: 660.0 [M+H]$^+$.

Example 18

(Z)-4-(4,4-dimethyl-3-(4-(4-(4-(methylsulfonyl)-3-(trifluoromethyl)phenyl)-1H-imidazol-1-yl)but-2-en-1-yl)-2,5-dioxoimidazolidin-1-yl)-2-(trifluoromethyl)benzonitrile Step A. (Z)-4-(3-(4-(4-Bromo-1H-imidazol-1-yl)but-2-en-1-yl)-4,4-dimethyl-2,5-dioxoimidazolidin-1-yl)-2-(trifluoromethyl)benzonitrile A mixture of (Z)-4-(3-(4-chlorobut-2-en-1-yl)-4,4-dimethyl-2,5-dioxoimidazolidin-1-yl)-2-(trifluoromethyl)benzonitrile (500 mg, 1.3 mmol), 4-bromo-1H-imidazole (191 mg, 1.3 mmol), and K$_2$CO$_3$ (359 mg, 2.6 mmol) in DMF (5 mL) was stirred at room temperature for 5 hours. The reaction mixture was poured into water (20 mL) and extracted with ethyl acetate (20 mL×3). The extracts were combined, washed with brine (30 mL), dried over sodium sulfate, filtered, and concentrated under reduced pressure to afford (Z)-4-(3-(4-(4-bromo-1H-imidazol-1-yl)but-2-en-1-yl)-4,4-dimethyl-2,5-dioxoimidazolidin-1-yl)-2-(trifluoromethyl)benzonitrile as a white solid (600 mg, 93%). LCMS (ESI) m/z: 496.1 [M+H]$^+$.

Step B. (Z)-4-(4,4-Dimethyl-3-(4-(4-(4-(methylsulfonyl)-3-(trifluoromethyl)phenyl)-1H-imidazol-1-yl)but-2-en-1-yl)-2,5-dioxoimidazolidin-1-yl)-2-(trifluoromethyl)benzonitrile A mixture of (Z)-4-(3-(4-(4-bromo-1H-imidazol-1-yl)but-2-en-1-yl)-4,4-dimethyl-2,5-dioxoimidazolidin-1-yl)-2-(trifluoromethyl)benzonitrile (500 mg, 1 mmol), 4,4,5,5-tetramethyl-2-(4-(methylsulfonyl)-3-(trifluoromethyl)phenyl)-1,3,2-dioxaborolane (350 mg, 1 mmol), K$_2$CO$_3$ (276 mg, 2 mmol), and Pd(PPh$_3$)$_4$ (55 mg, 0.046 mmol) in 1,4-dioxane (6 mL) and water (1 mL) under nitrogen atmosphere was stirred at 90° C. overnight. The reaction mixture was poured into water (10 mL) and extracted with ethyl acetate (20 mL×2). The extracts were combined, washed with brine (20 mL), dried over sodium sulfate, filtered, and concentrated under reduced pressure. The residue was purified by silica gel chromatography using petroleum ether: ethyl acetate (1:1) as eluting solvents to afford (Z)-4-(4,4-dimethyl-3-(4-(4-(4-(methylsulfonyl)-3-(trifluoromethyl)phenyl)-1H-imidazol-1-yl)but-2-en-1-yl)-2,5-dioxoimidazolidin-1-yl)-2-(trifluoromethyl)benzonitrile as a white solid (82 mg, 13%). $^1$HNMR (500 MHz, DMSO-d$_6$) δ (ppm) 8.33 (d, J=8.4 Hz, 1H), 8.28 (s, 1H), 8.24 (d, J=8.2 Hz, 1H), 8.22 (s, 1H), 8.19 (d, J=8.4 Hz, 1H), 8.17 (s, 1H), 8.06 (d, J=8.1 Hz, 1H), 7.89 (s, 1H), 5.76 (m, 2H), 4.90 (d, J=6.1 Hz, 2H), 4.24 (d, J=5.6 Hz, 2H), 3.29 (s, 3H), 1.51 (s, 6H); NOESY: There are correlations between 4.90 ppm (2H) and 8.17 & 7.89 ppm (two CH of imidazole); LCMS (ESI) m/z: 640.1 [M+H]$^+$.

Example 19

(Z)-4-(4,4-dimethyl-2,5-dioxo-3-(4-(4-phenyl-1H-1,2,3-triazol-1-yl)but-2-en-1-yl) imidazolidin-1-yl)-2-(trifluoromethyl)benzonitrile Step A. (Z)-4-(3-(4-azidobut-2-en-1-yl)-4,4-dimethyl-2,5-dioxoimidazolidin-1-yl)-2-(trifluoromethyl)benzonitrile A mixture of sodium azide (505 mg, 7.77 mmol), (Z)-4-(3-(4-chlorobut-2-en-1-yl)-4,4-dimethyl-2,5-dioxoimidazolidin-1-yl)-2-(trifluoromethyl)-benzonitrile (1.00 g, 2.59 mmol), in dry DMF (35 mL) was stirred at room temperature for 10 mn. The reaction mixture was diluted with ethyl acetate (100 mL), washed by water (30 mL×2) and by brine (30 mL), dried over sodium sulfate, filtered, and concentrated under reduced pressure to afford (Z)-4-(3-(4-azidobut-2-en-1-yl)-4,4-dimethyl-2,5-dioxoimidazolidin-1-yl)-2-(trifluoromethyl)benzonitrile as a yellow-orange oil (790 mg, 78%). LCMS (ESI) m/z: 505.11 [M+TFA]$^+$.

Step B. (Z)-4-(4,4-dimethyl-2,5-dioxo-3-(4-(4-phenyl-1H-1,2,3-triazol-1-yl)but-2-en-1-yl)imidazolidin-1-yl)-2-(trifluoromethyl)benzonitrile In a glass tube, to a mixture of freshly synthesized (Z)-4-(3-(4-azidobut-2-en-1-yl)-4,4-dimethyl-2,5-dioxoimidazolidin-1-yl)-2-(trifluoromethyl)benzonitrile (108 mg, 0.275 mmol) in toluene (1 mL) was added phenylacetylene (31 µL, 0.275 mmol) and DiPEA (50 µl, 0.275 mmol). The mixture was stirred at room temperature for 5 min and copper iodide (10 mg, 0.052 mmol) was added. The tube was sealed and stirred overnight. The reaction was diluted with dichloromethane (5 mL), absorbed to silica and the solvents were removed under reduced pressure. The absorbed residue was purified by silica gel chromatography using a gradient of heptane:ethyl acetate (0% to 80% in ethyl acetate) as eluting solvents to afford (Z)-4-(4,4-dimethyl-2,5-dioxo-3-(4-(4-phenyl-1H-1,2,3-triazol-1-yl)but-2-en-1-yl)imidazolidin-1-yl)-2-(trifluoromethyl)benzonitrile as a colorless resin (57 mg, 42%). $^1$HNMR (400 MHz, DMSO-d6) δ (ppm) 8.58 (s, 1H), 8.32 (d, J=8 Hz, 1H), 8.22 (s, 1H), 8.06 (d, J=8 Hz, 1H), 7.33-.7.85 (m, 5H), 5.82 (m, 2H), 5.28 (d, 2H), 4.26 (d, 2H), 1.50 (s, 6H); LCMS (ESI) m/z: 494.48 [(M+H]$^+$.

Example 20

(Z)-4-(3-(4-(4-(3,4-dichlorophenyl)-1H-1,2,3-triazol-1-yl)but-2-en-1-yl)-4,4-dimethyl-2,5-dioxoimidazolidin-1-yl)-2-(trifluoromethyl)benzonitrile Step A. (Z)-4-(3-(4-(4-(3,4-dichlorophenyl)-1H-1,2,3-triazol-1-yl)but-2-en-1-yl)-4,4-dimethyl-2,5-dioxoimidazolidin-1-yl)-2-(trifluoromethyl)benzonitrile In a glass tube, to a mixture of freshly synthesized (Z)-4-(3-(4-azidobut-2-en-1-yl)-4,4-dimethyl-2,5-dioxoimidazolidin-1-yl)-2-(trifluoromethyl)benzonitrile (108 mg, 0.275 mmol) in toluene (1 mL) was added 3,4 dichlorophenylacetylene (49 mg, 0.275 mmol) and DiPEA (50 µl, 0.275 mmol). The mixture was stirred at room temperature for 5 min and copper iodide (10 mg, 0.052 mmol) was added to the mixture. The tube was sealed and stirred overnight. The reaction was diluted with dichloromethane (5 mL), absorbed to silica gel and the solvents were removed under reduced pressure. The absorbed residue was purified by silica gel chromatography using a gradient of heptane:ethyl acetate (0% to 100% in ethyl acetate) as eluting solvents to afford (Z)-4-(3-(4-(4-(3,4-dichlorophenyl)-1H-1,2,3-triazol-1-yl)but-2-en-1-yl)-4,4-dimethyl-2,5-dioxoimidazolidin-1-yl)-2-(trifluoromethyl)benzonitrile as a white foam (92 mg, 59%). $^1$HNMR (400 MHz, DMSO-d6) δ (ppm) 8.73 (s, 1H), 8.32 (d, J=8 Hz, 1H), 8.21 (s, 1H), 8.06 (m, J=8 Hz, 2H), 7.70-0.7.86 (2d, 2H), 5.82 (m, 2H), 5.29 (d, J=5.4 Hz, 2H), 4.26 (d, J=4.8 Hz, 2H), 1.50 (s, 6H); LCMS (ESI) m/z: 563 [(M+H]$^+$ Example 21

((Z)-4-(3-(4-(4-(4-fluoro-3-methylphenyl)-1H-1,2,3-triazol-1-yl)but-2-en-1-yl)-4,4-dimethyl-2,5-dioxoimidazolidin-1-yl)-2-(trifluoromethyl)benzonitrile Step A. ((Z)-4-(3-(4-(4-(4-fluoro-3-methylphenyl)-1H-1,2,3-triazol-1-yl)but-2-en-1-yl)-4,4-dimethyl-2,5-dioxoimidazolidin-1-yl)-2-(trifluoromethyl)benzonitrile In a glass tube, to a mixture of freshly synthesized (Z)-4-(3-(4-azidobut-2-en-1-yl)-4,4-dimethyl-2,5-dioxoimidazolidin-1-yl)-2-(trifluoromethyl)benzonitrile (108 mg, 0.275 mmol) in toluene (1 mL) was added 1-Fluoro-2-methylphenylacetylene (38 µL, 0.275 mmol) and DiPEA (50 µL, 0.275 mmol). The mixture was stirred at room temperature for 5 min and copper iodide (10 mg, 0.052 mmol) was added to the mixture. The tube was sealed and stirred overnight. The reaction was diluted with dichloromethane (5 mL), absorbed to silica and the solvents were removed under reduced pressure. The absorbed residue was purified by silica gel chromatography using a gradient of heptane:ethyl acetate (0% to 80% in ethyl acetate) as eluting solvents to afford ((Z)-4-(3-(4-(4-(4-fluoro-3-methylphenyl)-1H-1,2,3-triazol-1-yl)but-2-en-1-yl)-4,4-dimethyl-2,5-dioxoimidazolidin-1-yl)-2-(trifluoromethyl)benzonitrile as a white solid (86 mg, 55%). 1HNMR (400 MHz, DMSO-d6) δ (ppm) 8.54 (s, 1H), 8.32 (d, J=8 Hz, 1H), 8.21 (s, 1H), 8.06 (d, J=8 Hz, 1H), 7.18-7.77 (3 m, 3H), 5.82 (m, 2H), 5.27 (d, J=5.2 Hz, 2H), 4.25 (d, J=4.8 Hz, 2H), 2.27 (s, 3H), 1.50 (s, 6H). LCMS (ESI) m/z: 527.1 [(M+H]$^+$.

Example 22

(Z)-4-(3-(4-(4-(4-cyano-3-(trifluoromethyl)phenyl)-1H-1,2,3-triazol-1-yl)but-2-en-1-yl)-4,4-dimethyl-2,5-dioxoimidazolidin-1-yl)-2-(trifluoromethyl)benzonitrile Step A. 2-(trifluoromethyl)-4-((trimethylsilyl)ethynyl)benzonitrile To a mixture of 4-iodo-2-(trifluoromethyl)benzonitrile (380 mg, 1.25 mmol) in tetrahydrofuran (8 mL) under nitrogen was added ethynyltrimethylsilane (256 µL, 2.5 mmol), copper iodide (50 mg, 0.25 mmol), triethylamine (530 µL, 3.75 mmol) and PdCl$_2$(Ph$_3$)$_2$ (42 mg, 0.06 mmol) and the mixture was stirred at room temperature overnight. The reaction mixture was poured into water (30 mL) and extracted with ethyl acetate (20 mL×3). The extracts were combined, washed with an aqueous solution of saturated Na2CO3 (20 mL), and brine (20 mL), dried over sodium sulfate, filtered, and concentrated under reduced pressure to provide a brown residue. The residue was purified by silica gel chromatography using a gradient of heptane:ethyl acetate (0% to 25% in ethyl acetate) as eluting solvents to afford (2-(trifluoromethyl)-4-((trimethylsilyl)ethynyl)benzonitrile as a colorless oil (300 mg, 90%). $^1$HNMR (400 MHz, DMSO-d6) δ (ppm) 8.16 (d, J=8 Hz, 1H), 8.03 (s, 1H), 7.94 (d, J=8 Hz, 1H), 0.26 (s, 9H), LCMS (ESI) m/z: no ionization, no ESI signal.

Step B. 4-ethynyl-2-(trifluoromethyl)benzonitrile

To a mixture of 2-(trifluoromethyl)-4-((trimethylsilyl)ethynyl)benzonitrile (1.3 g, 4.86 mmol) in methanol (25 mL) was added K$_2$CO$_3$ (1.18 g, 8.51 mmol) and the suspension was stirred at room temperature for 3 hours. The solvents are removed under moderate reduced pressure (expected product is volatile) and the residue was diluted in dichloromethane (10 mL) and washed with a aqueous solution of saturated Na$_2$CO$_3$ (10 mL), and then with brine (10 mL), dried over sodium sulfate, filtered, and concentrated under reduced pressure to provide 4-ethynyl-2-(trifluoromethyl)benzonitrile as a white solid (880 mg, 93%) which was used for next step without further purification. $^1$HNMR (400 MHz, DMSO-d6) δ (ppm) 8.19 (d, J=8 Hz, 1H), 8.08 (s, 1H), 7.99 (d, J=8 Hz, 1H), 4.80 (s, 1H), LCMS (ESI) m/z: no ionization, no ESI signal.

Step C. (Z)-4-(3-(4-(4-(4-cyano-3-(trifluoromethyl)phenyl)-1H-1,2,3-triazol-1-yl)but-2-en-1-yl)-4,4-dimethyl-2,5-dioxoimidazolidin-1-yl)-2-(trifluoromethyl)benzonitrile In a glass tube, to a mixture of freshly synthesized (Z)-4-(3-(4-azidobut-2-en-1-yl)-4,4-dimethyl-2,5-dioxoimidazolidin-1-yl)-2-(trifluoromethyl)benzonitrile (400 mg, 1.02 mmol) in toluene (5 mL) was added 4-ethynyl-2-(trifluoromethyl)benzonitrile (200 mg, 1.02 mmol) and DiPEA (180 µL, 1.02 mmol). The mixture was stirred at room temperature for 5 min and copper iodide (20 mg, 0.102 mmol) was added to the mixture. The tube was sealed and stirred overnight. The reaction was diluted with dichloromethane (20 mL), absorbed to silica and the solvents were removed under reduced pressure. The absorbed residue was purified by silica gel chromatography using a gradient of heptane:ethyl acetate (30% to 75% in ethyl acetate) as eluting solvents to afford (Z)-4-(3-(4-(4-(4-cyano-3-(trifluoromethyl)phenyl)-1H-1,2,3-triazol-1-yl)but-2-en-1-yl)-4,4-dimethyl-2,5-dioxoimidazolidin-1-yl)-2-(trifluoromethyl)benzonitrile as a white foam (246 mg, 41%). $^1$HNMR (400 MHz, DMSO-d6) δ (ppm) 8.99 (s, 1H), 8.04-8.39 (m, 6H), 5.83-5.85 (m, 2H), 5.33 (d, J=5.2 Hz, 2H), 4.26 (d, J=4.4 Hz, 2H), 1.51 (s, 6H). LCMS (ESI) m/z: 588 [(M+H]$^+$ Pharmacological Study of the Compounds According to the Invention Measurements of Anti-Proliferative Activities:

1. Anti-Proliferative Activity on LNCaP in Complete Medium

The anti-proliferative activity of the compounds of the present invention is determined on LNCaP in complete medium by applying the following experimental procedure:

The LNCaP cell type (ATCC, 1740) originates from a prostate carcinoma. This line expresses the androgen receptor and is hormone-dependent.

Maintenance of the LNCaP line is carried out in complete culture medium: RPMI, 10% of fetal calf serum, 2 mM glutamine, 100 U/ml penicillin, 0.1 mg/ml of streptomycin and 0.01M HEPES, 1 mM sodium pyruvate, 40% of D-glucose.

Seeding the plates:

The LNCaP line is seeded at 20,000 cells/well in 90 µl of complete medium in 96-well plates coated with poly-D-lysine (Biocoat, Costar).

Treatment of the cells: 24 h after the seeding, the cells are treated with 10 µl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 6 days, cell proliferation was determined by Cell-Titer-Glow (CTG) Luminescent Cell Viability Assay.

Results: The experiments are carried out in duplicate and the best compounds are tested twice. A concentration value inhibiting the cell proliferation by 50% ($IC_{50}$) is calculated.

All the compounds of Examples 1 to 22 described previously have an $IC_{50}$ of less than or equal to 5000 nM on the LNCaP cells in culture.

Among those, the compounds of the following examples have an $IC_{50}$ of less than 1500 nM on the LNCaP cells in culture: 1, 2, 3, 4, 5, 6, 7, 8, 9,11, 12, 13, 15, 16, 17, 18, 19, 21 and 22.

The compounds of the following examples have an $IC_{50}$ of less than 500 nM on the LNCaP cells in culture: 1, 2, 4, 5, 6 and 8

2. Anti-Proliferative Activity on DU145 in Complete Medium

DU145 is a prostate cancer cell line that does not express androgen receptor. It is used to evaluate the selectivity of the compounds for androgen receptor expressing cells. No activity of the compounds is expected.

The cells of the DU145 line (ATCC HTB-81) are seeded at 800 cells/well in 90 µl of complete medium in 96-well plates coated with poly-D-lysine (Biocoat, Costar).

Treatment of the cells: 24 h after the seeding, the cells are treated with 10 µl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 6 days, cell proliferation was determined by Cell-Titer-Glow (CTG) Luminescent Cell Viability Assay Results: The experiments are carried out in duplicate and the best compounds are tested twice. A concentration value inhibiting the cell proliferation by 50% ($IC_{50}$) is calculated.

The compounds of the following examples had no measurable IC50 on DU145 cells, meaning no anti-proliferative effect: 1, 2, 3, 4, 5, 6, 7, 8, 9, 10, 11, 12, 13, 14, 15, 16, 17.

3. Anti-Proliferative Activity on VCaP in Complete Medium

The cells of the VCaP line (ATCC CRL-2876) are seeded at 20000 cells/well in 90 µl of complete medium in 96-well plates coated with poly-D-lysine (Biocoat, Costar).

Treatment of the cells: 24 h after the seeding, the cells are treated with 10 µl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 9 days, cell proliferation was determined by Cell-Titer-Glow (CTG) Luminescent Cell Viability Assay Results: The experiments are carried out in duplicate and the best compounds are tested twice. A concentration value inhibiting the cell proliferation by 50% ($IC_{50}$) is calculated.

The compounds of Examples 1, 3, 4, 5, 6, 10, 11, 12, 13, 14, 15 and 16 described previously have an IC50 of less than or equal to 5000 nM on the VCaP cells in culture.

Among those, the compounds of the following examples have an IC50 of less than 1500 nM on the VCaP cells in culture: 1, 4, 5, 6, 11, 15 and 16

The compound of the example 5 has an IC50 of less than 500 nM on the VCaP cells in culture Measurement of Protein Expression of the Androgen Receptor The cells of the LNCaP line are seeded at a rate of 2.5 millions of cells per 10 cm Petri dish and maintained in 8 ml RPMI-1640 for 4 days. After 4 days incubation, 4 ml of medium were removed from the Petri dish and 5 ml fresh medium was added carefully. 1 ml of compounds 10-fold diluted in complete medium at concentrations from 3×10−6 M to 10−8 M. Cells were treated with the compounds for additional 3 days. The whole cell protein was extracted by Nuclear Extract kit and quantitated by the Bradford Protein Assay. The effect of compounds on AR levels in LNCaP cells was then determined by an AR ELISA kit. IC50 of Examples are listed below:

| Example No | IC50 AR destruction in LNCaP (nM) |
|---|---|
| 1 | 248 |
| 2 | 329 |
| 4 | 262 |
| 5 | 85 |

| Example No | IC50 AR destruction in LNCaP (nM) |
|---|---|
| 6 | 103 |
| 8 | 166 |
| 9 | 957 |
| 10 | 2014 |
| 11 | 195 |
| 14 | 988 |
| 15 | 297 |

The compounds of Examples 1, 2, 4, 5, 6, 8, 9, 10, 11, 14 and 15 described previously have an 1050 of less than or equal to 5000 nM on the AR destruction in LNCaP cells in culture.

Among those, the compounds of the following examples have an 1050 of less than 1500 nM on the AR destruction in LNCaP cells in culture 1, 2, 4, 5, 6, 8, 9, 11, 14 and 15.

The compound of the example 5 has an 1050 of less than 500 nM on the AR destruction in LNCaP cells in culture: 1, 2, 4, 5, 6, 8, 11 and 15

Evaluation of Solubility:

Test compounds were prepared as stock solutions at 100 mM in DMSO. The stock solutions were diluted, in duplicate, into 100 mM potassium phosphate buffer (pH 7.4) to a target concentration of 100 μM with a final DMSO concentration of 0.1%. The solutions were shaken at 1000 rpm for 1 hour at room temperature followed by centrifugation for 10 minutes at 1200 rpm to precipitate un-dissolved particles. The supernatants were transferred to new tubes and the samples were further prepared as follows:

Undiluted: 5 μL of supernatant to 95 μL of ACN containing internal standard (IS)

1:10 diluted: 10 μL of the supernatant into 90 μL K-buffer, mix, then transfer 5 μL of 1:10 diluted samples to 95 μL ACN containing IS 1:100 diluted: 10 μL of the supernatant into 990 μL K-buffer, mix, then transfer 5 μL of 1:100 diluted samples to 95 μL of ACN containing IS Samples (undiluted, 1:10 diluted, and 1:100 diluted) along with the standards were analyzed by LC-MS/MS.

Solubilities of Examples are listed below:

| Example No | Solubility (μM) |
|---|---|
| 3 | 0.2 |
| 4 | 1.7 |
| 5 | 0.65 |
| 6 | 4.38 |
| 11 | 0.34 |
| 14 | 24.1 |
| 15 | 1.895 |
| 17 | 1.97 |

The invention claimed is:
1. A compound of formula (I):

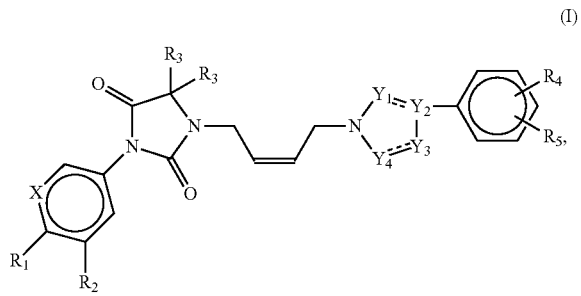

or a pharmaceutically acceptable salt thereof, wherein:
$R^1$ is —CN, —SO$_2$(C$_1$-C$_6$)alkyl, or —SO$_2$(C$_1$-C$_6$)cycloalkyl;
$R^2$ is —CF$_3$ or a halogen atom;
each $R^3$ is individually a (C$_1$-C$_6$)alkyl;
X is N;
$Y^1$ is an unsubstituted carbon atom or a carbon atom that is substituted by one or more (C$_1$-C$_6$) alkyl groups;
$Y^2$ is an unsubstituted carbon atom or a carbon atom that is substituted by a —OH group;
$Y^3$ is an unsubstituted carbon atom or a carbon atom substituted by one or more (C$_1$-C$_6$) alkyl groups;
$Y^4$ is an unsubstituted nitrogen atom or a nitrogen atom substituted by one or more (C$_1$-C$_6$) alkyl groups;
$R^4$ is H, alkyl, a halogen, —CN, or a —SO$_2$(C$_1$-C$_6$)alkyl group;
$R^5$ is H, —CF$_3$, a (C$_1$-C$_6$) alkyl group, or a halogen atom; and
each ═ is a double bond.

2. The compound of claim 1, wherein $R^1$ is a —SO$_2$(C$_1$-C$_6$) alkyl group.
3. The compound of claim 1, wherein $R^1$ is a —CN group.
4. The compound of claim 1, wherein $R^2$ is —CF$_3$.
5. The compound of claim 1, wherein $R^4$ is a —SO$_2$(C$_1$-C$_6$) alkyl group.
6. The compound of claim 1, wherein $R^5$ is a —CF$_3$ group.
7. The compound of claim 1, which is:
(Z)-5-(4,4-dimethyl-3-(4-(4-(4-(methylsulfonyl)3-(trifluoromethyl)phenyl)-1H-pyrazol-1-yl)but-2-en-1-yl)-2,5-dioxoimidazolidin-1-yl)-3-(trifluoromethyl)picolinonitrile, or a pharmaceutically acceptable salt thereof; or
(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile, or a pharmaceutically acceptable salt thereof.
8. The compound of claim 1, which is
(Z)-5-(3-(4-(4-(3-chloro-4-(methylsulfonyl)phenyl)-1H-pyrazol-1-yl)but-2-en-1-yl)-4,4-dimethyl-2,5-dioxoimidazolidin-1-yl)-3-(trifluoromethyl)picolinonitrile, or a pharmaceutically acceptable salt thereof.
9. A pharmaceutical composition comprising a compound of claim 1 and a pharmaceutically acceptable support.
10. The compound of claim 1, wherein $R^3$ is a methyl group.

* * * * *